United States Patent [19]
Rane et al.

[11] Patent Number: 5,958,890
[45] Date of Patent: Sep. 28, 1999

[54] TRICYCLIC COMPOUNDS USEFUL FOR INHIBITION OF G-PROTEIN FUNCTION AND FOR TREATMENT OF PROLIFERATIVE DISEASES

[75] Inventors: Dinanath F. Rane, Morganville; Alan K. Mallams, Hackettstown; Arthur G. Taveras, Rockaway; F. George Njoroge, Union, all of N.J.

[73] Assignee: Schering Corporation, Kenilworth, N.J.

[21] Appl. No.: 08/927,727

[22] Filed: Sep. 11, 1997

Related U.S. Application Data

[60] Provisional application No. 60/025,248, Sep. 13, 1996.

[51] Int. Cl.⁶ .......................... A61K 31/70; A61K 31/44; C07M 15/00; C07D 221/16
[52] U.S. Cl. ............................. 514/43; 514/23; 514/253; 514/256; 514/275; 514/284; 514/290; 536/18.7; 536/22.1; 544/238; 544/361; 544/405; 546/93
[58] Field of Search ..................................... 514/253, 254, 514/256, 269, 275, 289, 290, 295, 23, 25, 93; 544/295, 298, 238, 322, 333, 361, 405; 546/93; 536/18.7, 22.1

[56] References Cited

U.S. PATENT DOCUMENTS

| | | |
|---|---|---|
| 4,826,853 | 5/1989 | Piwinski et al. . |
| 5,089,496 | 2/1992 | Piwinski et al. . |
| 5,151,423 | 9/1992 | Piwinski et al. . |
| 5,393,890 | 2/1995 | Syoji et al. . |

FOREIGN PATENT DOCUMENTS

| | | |
|---|---|---|
| WO95/10514 | 4/1995 | WIPO . |
| WO95/10515 | 4/1995 | WIPO . |
| WO95/10516 | 4/1995 | WIPO . |
| WO96/30363 | 10/1996 | WIPO . |
| WO97/23478 | 7/1997 | WIPO . |

OTHER PUBLICATIONS

Nielsen, et al, *J. Med. Chem.*, 33(1990), pp. 71–77.
Haake, et al, *Synthesis*(1991), pp. 753–758.
Kloek et al, *J. Org. Chem.*, 41(25) (1976), pp. 4028–4029.
Cassal et al, *Helv. Chim. Acta*, 59 (6) (197677), pp. 1917–1924.
Buschauer, *Arch. Pharm.*, 320 (1987), pp. 377–378.
Appel et al, *Chem. Ber.*, 91 (1958), pp. 1339–1341.
Winograd, *Oxford Textbook of Oncology*, vol. 1 (Oxford U. Press, Oxford), ed. by Beckham et al, pp. 486–495 (1995).

*Primary Examiner*—Elli Peselev
*Attorney, Agent, or Firm*—Anita W. Magatti

[57] ABSTRACT

Compounds the formula

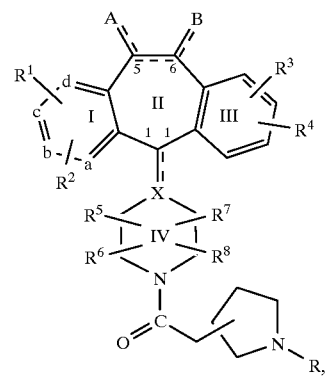

their use as farnesyl transferase protein inhibitors and pharmaceutical compositions containing them are disclosed, especially compounds of the formula

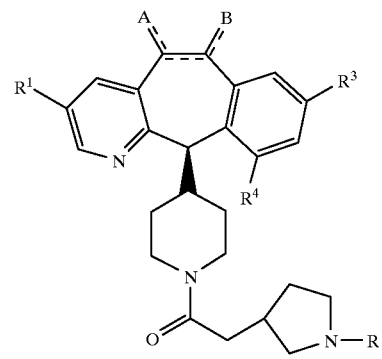

wherein $R^1$, $R^2$ and $R^3$ are halo, A and B are each $H_2$, and R is as defined in the specification.

16 Claims, No Drawings

TRICYCLIC COMPOUNDS USEFUL FOR INHIBITION OF G-PROTEIN FUNCTION AND FOR TREATMENT OF PROLIFERATIVE DISEASES

It is hereby claimed the benefit under Title 35, United States Code, §119(e) of U.S. provisional application 60/025,248, filed on Sep. 13, 1996.

BACKGROUND

WO 95/10516, published Apr. 20, 1995 discloses tricyclic compounds useful for inhibiting farnesyl protein transferase.

In view of the current interest in inhibitors of farnesyl protein transferase, a welcome contribution to the art would be compounds useful for the inhibition of farnesyl protein transferase. Such a contribution is provided by this invention.

SUMMARY OF THE INVENTION

This invention provides compounds useful for the inhibition of farnesyl protein transferase (FPT). The compounds of this invention are represented by the formula:

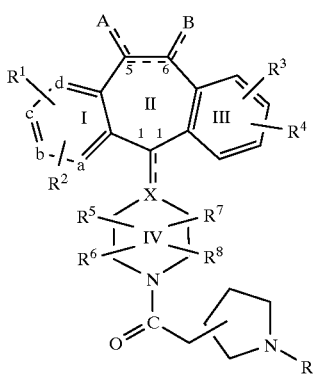

(1.0)

or a pharmaceutically acceptable salt or solvate thereof, wherein: one of a, b, c and d represents N or $NR^9$ wherein $R^9$ is O—, —$CH_3$ or —$(CH_2)_nCO_2H$ wherein n is 1 to 3, and the remaining a, b, c and d groups represent $CR^1$ or $CR^2$; or each of a, b, c, and d are independently selected from $CR^1$ or $CR^2$;

each $R^1$ and each $R^2$ is independently selected from H, halo, —$CF_3$, —$OR^{10}$ (e.g., —$OCH_3$), —$COR^{10}$, —$SR^{10}$ (e.g., —$SCH_3$ and —$SCH_2C_6H_5$), —$S(O)_tR^{11}$ (wherein t is 0, 1 or 2, e.g., —$SOCH_3$ and —$SO_2CH_3$), —SCN, $N(R^{10})_2$, —$NR^{10}R^{11}$, —$NO_2$, —$OC(O)R^{10}$, —$CO_2R^{10}$, —$OCO_2R^{11}$, —CN, —$NHC(O)R^{10}$, —$NHSO_2R^{10}$, —$CONHR^{10}$, —$CONHCH_2CH_2OH$, —$NR^{10}COOR^{11}$,

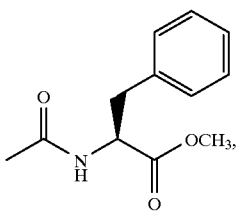

—$SR^{11}C(O)OR^{11}$ (e.g., —$SCH_2CO_2CH_3$), —$SR^{11}N(R^{75})_2$ wherein each $R^{75}$ is independently selected from H and —$C(O)OR^{11}$ (e.g., —$S(CH_2)_2NHC(O)O$-t-butyl and —$S(CH_2)_2NH_2$), benzotriazol-1-yloxy, tetrazol-5-ylthio, or substituted tetrazol-5-ylthio (e.g., alkyl substituted tetrazol-5-ylthio such as 1-methyl-tetrazol-5-ylthio), alkynyl, alkenyl or alkyl, said alkyl or alkenyl group optionally being substituted with halo, —$OR^{10}$ or —$CO_2R^{10}$;

$R^3$ and $R^4$ are independently selected from the group consisting of H, R and $R^{2}$, or $R^3$ and $R^4$ taken together represent a saturated or unsaturated $C_5$–$C_7$ fused ring to the benzene ring (Ring III);

$R^5$, $R^6$, $R^7$ and $R^8$ are independently selected from the group consisting of H, —$CF_3$, —$COR^{10}$, alkyl and aryl, said alkyl or aryl optionally being substituted with —$OR^{10}$, —$SR^{10}$, —$S(O)_tR^{11}$, —$NR^{10}COOR^{11}$, —$N(R^{10})_2$, —$NO_2$, —$COR^{10}$, —$OCOR^{10}$, —$OCO_2R^{11}$, —$CO_2R^{10}$ or $OPO_3R^{10}$, or $R^5$ is combined with $R^6$ to represent =O or =S, or $R^7$ is combined with $R^8$ to represent =O or =S;

$R^{10}$ represents H, alkyl, aryl, or aralkyl (e.g., benzyl);

$R^{11}$ represents alkyl or aryl;

X represents N, CH or C, which C may contain an optional double bond (represented by the dotted line) to carbon atom 11;

the dotted line between carbon atoms 5 and 6 represents an optional double bond, such that when a double bond is present, A and B independently represent —$R^{10}$, halo, —$OR^{11}$, —$OCO_2R^{11}$ or —$OC(O)R^{10}$, and when no double bond is present between carbon atoms 5 and 6, A and B each independently represent (H, H), (—$OR^{11}$, —$OR^{11}$), (H, halo), (halo, halo), (alkyl, H), (alkyl, alkyl), (H, —OC(O) $R^{10}$), (H, —$OR^{10}$), =O , (aryl, H) or =$NOR^{10}$, or A and B together are —O—$(CH_2)_p$—O— wherein p is 2, 3 or 4; and R represents:

(1) —$C(O)N(R^{10})_2$;

(2) —$CH_2C(O)N(R^{10})_2$;

(3) —$SO_2$-alkyl, —$SO_2$-aryl, —$SO_2$-aralkyl, —$SO_2$-heteroaryl or —$SO_2$-heterocycloalkyl;

(4) cyano (i.e., CN);

(5) an imidate represented by the formula:

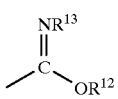

wherein $R^{13}$ is selected from the group consisting of H, CN, —$SO_2$-alkyl (e.g., —$SO_2CH_3$), —C(O)-aryl (e.g., —C(O) $C_6H_5$, i.e., —C(O)phenyl), —$SO_2NR^{10}R^{14}$ (e.g., —$SO_2NH_2$), —$C(O)NR^{10}R^{14}$ (e.g., —$C(O)NH_2$) and —$OR^{10}$ (e.g., OH and —$OCH_3$); $R^{12}$ is aryl; and $R^{14}$ is independently selected from the group consisting of H, alkyl, aryl and aralkyl;

(6) an imidamido group of the formula:

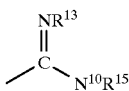

wherein $R^{10}$ and $R^{13}$ are as defined above; $R^{15}$ is alkyl, aryl, aralkyl, cycloalkyl, heteroaryl, heteroaralkyl or heterocycloalkyl;

(7) a 1-amino-2-nitroethylene derivative of the formula:

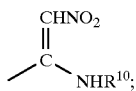

(8) —C(O)$R^{16}$, wherein $R^{16}$ is alkyl, aryl, aralkyl or heteroaryl;
(9) —C(O)—O—$R^{16}$;
(10)

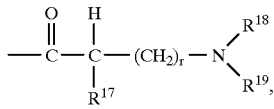

wherein $R^{17}$ is selected from the group consisting of H, alkyl, aralkyl (e.g., benzyl) and heteroaralkyl (e.g., —$CH_2$-imidazolyl); $R^{18}$ and $R^{19}$ are each independently selected from the group consisting of: H; —C(O)O$R^{20}$, wherein $R^{20}$ represents alkyl, aralkyl, and heteroaralkyl; —$SO_2R^{21}$ wherein $R^{21}$ is selected from the group consisting of alkyl (e.g., $C_{1-6}$ alkyl, such as methyl), aryl, aralkyl, heteroaryl and heteroaralkyl; —C(O)$R^{21}$; $C_{1-6}$ alkyl; alkaryl; and $C_{3-6}$ cycloalkyl; and r is 0, 1 or 2;

(11) alkyl, aryl. aralkyl, cycloalkyl, heterocycloalkyl or heteroaryl;
(12) —$SO_2NR^{10}R^{14}$;
(13) —P(O)($R^{10}$)$_2$;
(14) a sugar group of the formula

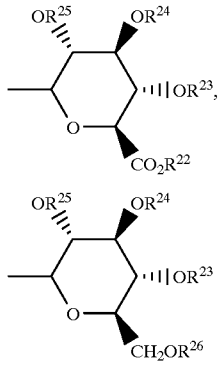

or

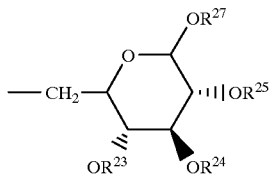

wherein $R^{22}$ and $R^{26}$ are independently selected from the group consisting of H, ($C_{1-6}$)alkyl, aryl and aryl($C_1$–$C_6$) alkyl; and $R^{23}$, $R^{24}$, $R^{25}$ and $R^{27}$ are independently selected from the group consisting of H, ($C_1$–$C_6$)alkyl, aryl($C_1$–$C_6$) alkyl, —C(O)($C_1$–$C_6$)alkyl and —C(O)aryl; or

(15) —$CH_2C(O)OR^{28}$, wherein $R^{28}$ is selected from the group consisting of H, alkyl (e.g., —C($CH_3$)$_3$), aryl and heteroaryl.

The compounds of this invention: (i) potently inhibit farnesyl protein transferase, but not geranylgeranyl protein transferase I, in vitro; (ii) block the phenotypic change induced by a form of transforming Ras which is a farnesyl acceptor but not by a form of transforming Ras engineered to be a geranylgeranyl acceptor; (iii) block intracellular processing of Ras which is a farnesyl acceptor but not of Ras engineered to be a geranylgeranyl acceptor; and (iv) block abnormal cell growth in culture induced by transforming Ras.

The compounds of this invention inhibit farnesyl protein transferase and the farnesylation of the oncogene protein Ras. Thus, this invention further provides a method of inhibiting farnesyl protein transferase, (e.g., ras farnesyl protein transferase) in mammals, especially humans, by the administration of an effective amount of the tricyclic compounds described above. The administration of the compounds of this invention to patients, to inhibit farnesyl protein transferase, is useful in the treatment of the cancers described below.

This invention provides a method for inhibiting or treating the abnormal growth of cells, including transformed cells, by administering an effective amount of a compound of this invention. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

This invention also provides a method for inhibiting or treating tumor growth by administering an effective amount of the tricyclic compounds, described herein, to a mammal (e.g., a human) in need of such treatment. In particular, this invention provides a method for inhibiting or treating the growth of tumors expressing an activated Ras oncogene by the administration of an effective amount of the above described compounds. Examples of tumors which may be inhibited or treated include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma and epidermal carcinoma.

It is believed that this invention also provides a method for inhibiting or treating proliferative diseases, both benign and malignant, wherein Ras proteins are aberrantly activated as a result of oncogenic mutation in other genes—i.e., the Ras gene itself is not activated by mutation to an oncogenic form—with said inhibition or treatment being accomplished by the administration of an effective amount of the tricyclic compounds described herein, to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn), may be inhibited or treated by the tricyclic compounds described herein.

The tricyclic compounds useful in the methods of this invention inhibit or treat the abnormal growth of cells. Without wishing to be bound by theory, it is believed that these compounds may function through the inhibition of G-protein function, such as ras p21, by blocking G-protein isoprenylation, thus making them useful in the treatment of proliferative diseases such as tumor growth and cancer. Without wishing to be bound by theory, it is believed that these compounds inhibit ras farnesyl protein transferase, and thus show antiproliferative activity against ras transformed cells.

DETAILED DESCRIPTION OF THE INVENTION

As used herein, the following terms are used as defined below unless otherwise indicated:

M+—represents the molecular ion of the molecule in the mass spectrum;

MH+—represents the molecular ion plus hydrogen of the molecule in the mass spectrum;

benzotriazol-1-yloxy represents

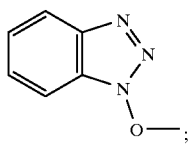

1-methyl-tetrazol-5-ylthio represents

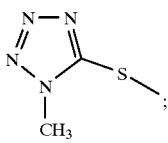

alkyl (including the alkyl portions of alkoxy, alkylamino and dialkylamino) represents straight and branched carbon chains and contains from one to twenty carbon atoms, preferably 1 to 6 carbon atoms;

alkenyl represents straight and branched carbon chains having at least one carbon to carbon double bond and containing from 2 to 12 carbon atoms, preferably from 2 to 6 carbon atoms and most preferably from 3 to 6 carbon atoms;

alkynyl represents straight and branched carbon chains having at least one carbon to carbon triple bond and containing from 2 to 12 carbon atoms, preferably from 2 to 6 carbon atoms;

aralkyl—represents an aryl group, as defined below, bound to an alkyl group, as defined above, wherein preferably the alkyl group is —CH$_2$—, (e.g., benzyl);

aryl represents a carbocyclic group containing from 6 to 15 carbon atoms and having at least one aromatic ring (e.g., aryl is a phenyl ring), with all available substitutable carbon atoms of the carbocyclic group being intended as possible points of attachment, said carbocyclic group being optionally substituted (e.g., 1 to 3) with one or more of halo, alkyl, hydroxy, alkoxy, phenoxy, CF$_3$, amino, alkylamino, dialkylamino, —COOR$^{12}$ or —NO$_2$;

cycloalkyl represents saturated carbocyclic rings branched or unbranched of from 3 to 20 carbon atoms, preferably 3 to 7 carbon atoms;

halo represents fluoro, chloro, bromo and iodo;

heteroaryl—represents cyclic groups, optionally substituted with R$^3$ and R$^4$, having at least one heteroatom selected from O, S or N, said heteroatom interrupting a carbocyclic ring structure and having a sufficient number of delocalized pi electrons to provide aromatic character, with the aromatic heterocyclic groups preferably containing from 2 to 14 carbon atoms, e.g., (1) thienyl (e.g., 2- or 3-thienyl), (2) imidazolyl (e.g., (2-, 4- or 5-) imidazolyl), (3) triazolyl (e.g., 3- or 5- [1,2,4-triazolyl]), (4) tetrazolyl, (5) substituted tetrazolyl, such as

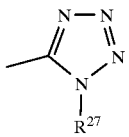

wherein R$^{27}$ represents aryl (e.g., phenyl), alkyl (e.g., —CH$_3$) or arylalkyl (e.g., benzyl), (6) furyl (e.g., 2- or 3-furyl), (7) thiazolyl (or thiazyl), (8) pyrimidinyl, (9) pyrazinyl (e.g., 2-pyrazinyl), (10) pyridazinyl (e.g., 3- or 4-pyridazinyl), (11) triazinyl, (12) thiadiazolyl], (13) 2-, 3-, 4-, 5-, 6- or 7-benzofuranyl, (14) benzoxazolyl (e.g., 2-, 4-, 5-, 6- or 7-benzoxazolyl), (15) indolyl (benzopyrrolyl) (e.g., 2-, 3-, 4-, 5-, 6- or 7-indolyl), (16) pyrazolyl (e.g., 3-, 4- or 5-pyrazolyl), (17) oxazolyl (e.g., 2-, 4- or 5-oxazolyl), (18) 2-, 3- or 4-pyridyl or pyridyl N-oxide (optionally substituted with R$^3$ and R$^4$), wherein pyridyl N-oxide can be represented as:

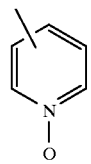

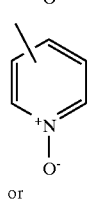

or

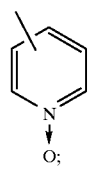

(19) isoxazolyl, (20) benzisoxazolyl, (21) pyrrolyl, (22) benzimidazolyl, (23) isoquinolinyl, (24) quinolinyl, (25) pyridopyrazinyl, (26) pyranyl, (27) benzothienyl, (28) isobenzofuranyl or (29) isothiazolyl;

heteroarylalkyl (heteroaralkyl)—represents a heteroaryl group, as defined above, bound to an alkyl group, as defined above, preferably the alkyl group is —CH$_2$—, for example, —CH$_2$—(4- or 5-)imidazolyl;

heterocycloalkyl—represents a saturated, branched or unbranched carbocylic ring containing from 3 to 15 carbon atoms, preferably from 4 to 6 carbon atoms, which carbocyclic ring is interrupted by 1 to 3 hetero groups selected from —O—, —S—, —NR$^{10}$— (wherein R$^{10}$ is as defined above); suitable heterocycloalkyl groups include: (1) tetrahydrofuranyl (e.g., 2- or 3-tetrahydrofuranyl), (2) tetrahydrothienyl e.g., (2- or 3- tetrahydrothienyl), (3) piperidinyl (e.g., 2-, 3- or 4-piperidinyl), (4) pyrrolidinyl (e.g., 2- or 3-pyrrolidinyl), (5) 2- or 3-piperizinyl, (6) 2- or 4-dioxanyl, (7) tetrahydopyranyl and (8) morpholinyl.

The following solvents and reagents are referred to herein by the abbreviations indicated: ethanol (EtOH); ethyl acetate (EtOAc); N,N-dimethylformamide (DMF); trifluoroacetic acid (TFA); N-methylmorpholine (NMM); 1-hydroxybenzotriazole (HOBT); triethylamine (Et₃N); and 1-(3-dimethylaminopropyl)-3-ethyl carbodiimde hydrochloride (DEC).

Reference to the position of the substituents $R^1$, $R^2$, $R^3$, and $R^4$ is based on the numbered ring structure:

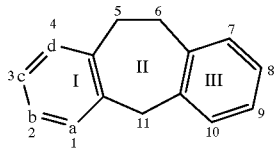

Preferably, compounds of Formula 1.0 are represented by compounds of Formula 1.1:

(1.1)

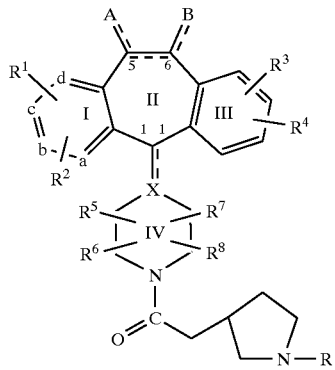

wherein the substituents are as defined for Formula 1.0.

Compounds of Formula 1.0 include compounds wherein $R^2$ and $R^4$ are H, and $R^1$ and $R^3$ are halo (preferably independently selected from Br or Cl). For example, $R^1$ is Br and $R^3$ is Cl. These compounds include compounds wherein $R^1$ is in the 3-position and $R^3$ is in the 8-position, e.g., 3-Br and 8-Cl. Compounds of Formula 1.0 also include compounds wherein $R^2$ is H, and $R^1$, $R^3$ and $R^4$ are halo (preferably independently selected from Br or Cl).

Preferably, $R^2$ is H and $R^1$, $R^3$ and $R^4$ are halo; a is N and b, c and d are carbon; A and B are each H₂; the optional bond between C5 and C6 is absent; X is CH; and $R^5$, $R^6$, $R^7$ and $R^8$ are H. More preferably, $R^1$, $R^3$ and $R^4$ are independently selected from Br or Cl. Still more preferably, $R^2$ is H, $R^1$ is Br, and $R^3$ and $R^4$ are independently selected from Cl and Br.

More preferably, compounds of Formula 1.0 are represented by compounds of Formula 1.2 and Formula 1.3:

(1.2)

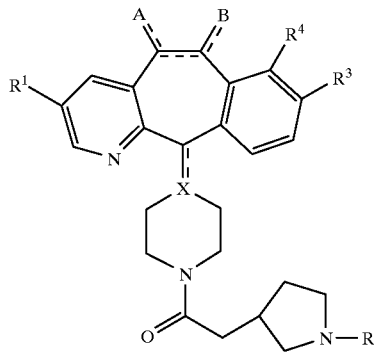

(1.3)

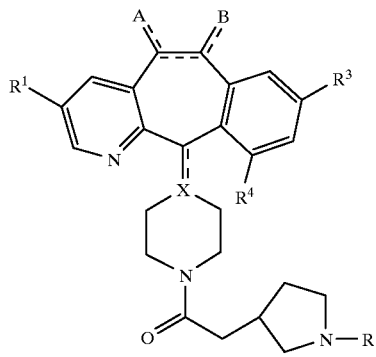

wherein $R^1$, $R^3$ and $R^4$ are each independently selected from halo, preferably, Br or Cl; and A, B, X and W are as defined for Formula 1.0. More preferably, A and B are each H₂; the optional bond between C5 and C6 is absent; and X is CH. Most preferably, $R^1$ is Br; $R^3$ and $R^4$ are independently Br or Cl, and still more preferably $R^3$ is Cl and $R^4$ is Cl or Br; A and B are each H₂; the optional bond between C5 and C6 is absent; and X is CH.

In the definition of R, in general, a preferred definition of aryl is phenyl, a preferred definition of aralkyl is benzyl, and preferred heteroaryl and heterocycloalkyl groups are as exemplified above.

Examples of —C(O)NR¹⁰R¹¹ substituents are those wherein $R^{10}$ and $R^{11}$ are H or alkyl.

Examples of —CH₂C(O)NR¹¹R¹¹ substituents are those wherein $R^{10}$ and $R^{11}$ are H or alkyl.

Examples of imidates for substituent R include groups wherein $R^{13}$ is: (1) CN; (2) H; (3) —SO₂NR¹⁰R¹⁴ wherein $R^{10}$ and $R^{14}$ are selected from the group consisting of: H and alkyl (e.g., methyl); (4) —C(O)NR¹⁰R¹⁴ wherein $R^{10}$ and $R^{14}$ are selected from the group consisting of: H and alkyl (e.g., methyl); (5) —SO₂-alkyl; or (6) —C(O)-aryl. Examples of imidates also include groups wherein $R^{12}$ is phenyl.

For example, imidates for substituent R include groups wherein $R^{13}$ is selected from the group consisting of: CN, —C(O)NH₂, H, —SO₂NH₂, —SO₂NHCH₃, —SO₂N(CH₃)₂, —C(O)NHCH₃, —SO₂CH₃ and —C(O)C₆H₅. Exampes of imidates also include groups wherein $R^{12}$ is phenyl and $R^{13}$ is selected from the group consisting of: CN, —C(O)NH₂, H, —SO₂NH₂, —SO₂NHCH₃, —SO₂N(CH₃)₂, —C(O)NHCH₃, —SO₂CH₃ and —C(O)C₆H₅.

Examples of imidamido groups for substituent R include groups wherein $R^{13}$ is selected from the group consisting of:

(1) CN; (2) H; (3) —OR$^{10}$; (4) —SO$_2$NR$^{10}$R$^{14}$ wherein R$^{10}$ and R$^{14}$ are independently selected from the group consisting of: H and alkyl (e.g., methyl), (5) —C(O)NR$^{10}$R$^{14}$ wherein R$^{10}$ and R$^{14}$ are independently selected from the group consisting of: H and alkyl (e.g., methyl); (6) —SO$_2$-alkyl; and (7) —C(O)-aryl. Examples of the imidamido groups also include groups wherein R$^{10}$ and R$^{14}$ shown in the imidamido structure (i.e., not the R$^{10}$ and R$^{14}$ which are part of R$^{13}$) are selected from the group consisting of H and alkyl (e.g., —CH$_3$) and wherein R$^{14}$ is H or heteroaralkyl (e.g., 3-pyridylmethyl).

For example, imidamido groups for substituent R include groups wherein R$^{13}$ is selected from the group consisting of: CN, H, —OCH$_3$, —OH, —SO$_2$NH$_2$, —SO$_2$NHCH$_3$, —SO$_2$N(CH$_3$)$_2$, —C(O)NH$_2$, —C(O)NHCH$_3$, —SO$_2$CH$_3$ and —C(O)C$_6$H$_5$. Examples of imidamido groups also include groups wherein R$^{10}$ and R$^{14}$ are selected from the group consisting of: H and

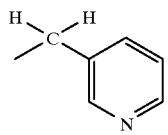

(i.e., 3-pyridylmethyl).

Examples of the imidamido substituents additionally include groups wherein: R$^{10}$ and R$^{14}$ are selected from the group consisting of H and 3-pyridylmethyl; and R$^{13}$ is selected from the group consisting of: CN, H, —OCH$_3$, —OH, —SO$_2$NH$_2$, —SO$_2$NHCH$_3$, —SO$_2$N(CH$_3$)$_2$, —C(O)NH$_2$, —C(O)NHCH$_3$, —SO$_2$CH$_3$ and —C(O)C$_6$H$_5$.

In addition, examples of the imidamido substituents additionally include groups wherein: (1) R$^{13}$ and R$^{10}$ are H, and R$^{14}$ is 3-pyridylmethyl; and (2) R$^{10}$ and R$^{14}$ are H, and R$^{13}$ is selected from the group consisting of: CN, H, —OCH$_3$, —OH, —SO$_2$NH$_2$, —SO$_2$NHCH$_3$, —SO$_2$N(CH$_3$)$_2$, —C(O)NH$_2$, —C(O)NHCH$_3$, —SO$_2$CH$_3$ and —C(O)C$_6$H$_5$.

Examples of 1-amino-2-nitroethylene derivatives for substituent R include groups wherein R$^{10}$ is alkyl, e.g., methyl.

When R is —COR$^{16}$, R$^{16}$ is preferably alkyl, e.g., methyl, or aralkyl, e.g., benzyl; examples of R$^{16}$ heteroatyl groups are pyridyl, indolyl, pyrrolyl and N-substituted pyrrolyl (e.g., N-alkylpyrrolyl such as N-alkylpyrrol-2-yl, such as, N-methylpyrrol-2-yl). When R is —C(O)O—R$^{16}$, R$^{16}$ is preferably alkyl, e.g., methyl, or aralkyl, e.g., benzyl.

When R is

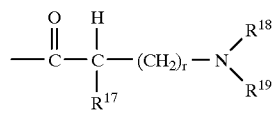

and r is O, R$^{17}$ is preferably H, alkyl, aralkyl or heteroaralkyl, and R$^{18}$ and R$^{19}$ are preferably H, —C(O)OR$^{20}$ wherein R$^{20}$ is alkyl, —SO$_2$R$^{21}$ wherein R$^{21}$ is alkyl, —C(O)R$^{21}$ wherein R$^{21}$ is aryl or alkyl; when r is 1 or 2, R$^{17}$ is preferably H and R$^{18}$ and R$^{19}$ are preferably alkyl.

When R is —SO$_2$NR$^{10}$R$^{14}$, R$^{10}$ and R$^{14}$ are preferably H or alkyl.

When R is —P(O)(R$^{10}$)$_2$, R$^{10}$ is preferably alkyl.

When R is a sugar, it preferably has the formula

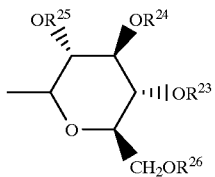

wherein R$^{23}$, R$^{24}$, R$^{25}$ and R$^{26}$ are —C(O)alkyl, especially acetyl.

Preferred R groups are —C(O)N(R$^{10}$)$_2$, —CH$_2$C(O)N(R$^{10}$)$_2$ wherein R$^{10}$ is preferably H, and —SO$_2$-alkyl, preferably —SO$_2$CH$_3$.

Compounds of Formulas 1.2A and 1.3B:

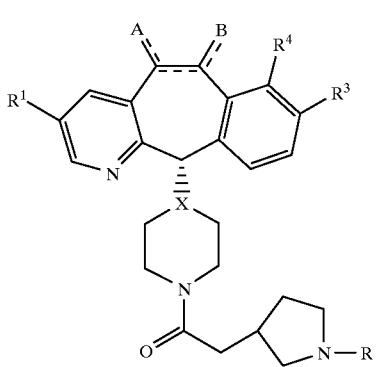

(1.2A)

and

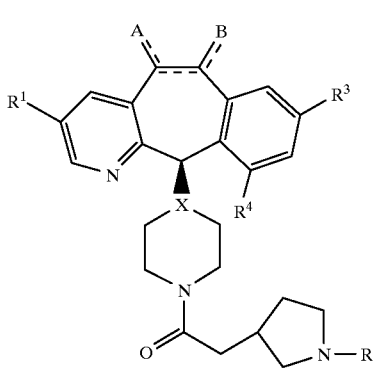

(1.3A)

are preferred when X is CH or N, and R$^1$, R$^3$ and R$^4$ are halo.

The preferred compounds of this invention are represented by the compounds of Formulas:

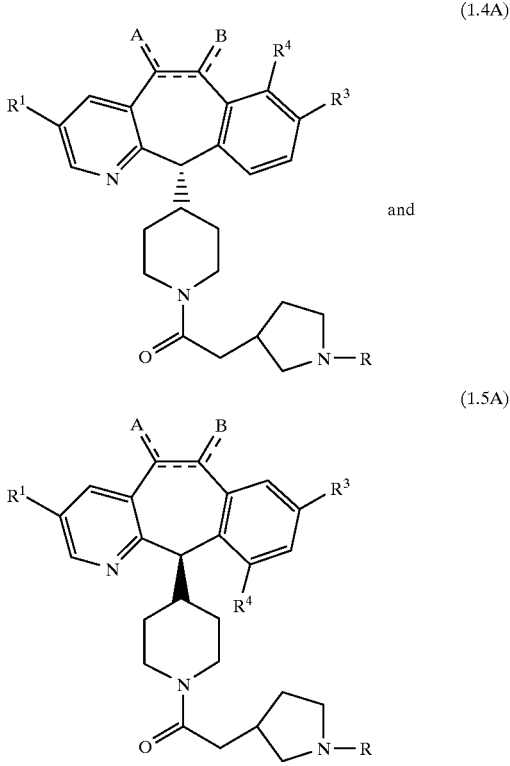

(1.4A)

and (1.5A)

wherein $R^1$, $R^3$ and $R^4$ are halo and the remaining substituents are as defined above, with compounds of Formula 1.5A being more preferred.

Lines drawn into the ring systems indicate that the indicated bond may be attached to any of the substitutable ring carbon atoms.

Certain compounds of the invention may exist in different isomeric (e.g., enantiomers and diastereoisomers) forms. The invention contemplates all such isomers both in pure form and in admixture, including racemic mixtures. Enol forms are also included.

Certain tricyclic compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic tricyclic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

Compounds of the invention may be prepared according to the procedures described in WO 95/10516 published Apr. 20, 1995, copending application Ser. No. 08/410,187 filed Mar. 24, 1995, copending application Ser. No. 08/577,951 filed Dec. 22, 1995, and co-pending application Ser. No. 08/615,760, filed Mar. 13, 1996, the disclosures of each being incorporated herein by reference thereto; and according to the procedures described below.

Compounds of the invention can be prepared by reacting a compound of the formula:

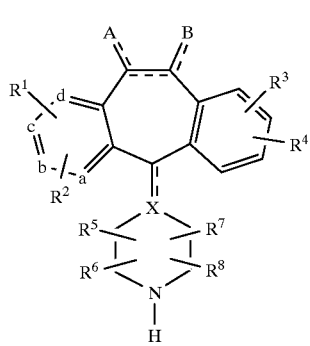

(19.0)

wherein all substituents are as defined for Formula 1.0, with 1-N-t-butoxycarbonylpyrrolidinyl acetic acid under standard coupling conditions e.g., at room temperature in a solvent such as DMF and in the presence of coupling agents such as DEC, HOBT and N-methylmorpholine, to produce a compound of the formula:

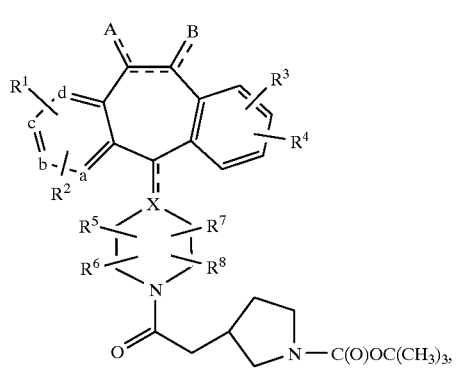

(20.0)

or by reacting a compound of Formula 19.0 with N-boc-homoproline methyl ester under standard coupling conditions e.g., at room temperature in a solvent such as DMF and in the presence of coupling agents such as DEC, HOBT and N-methylmorpholine, to produce a compound of the formula:

(20.1)

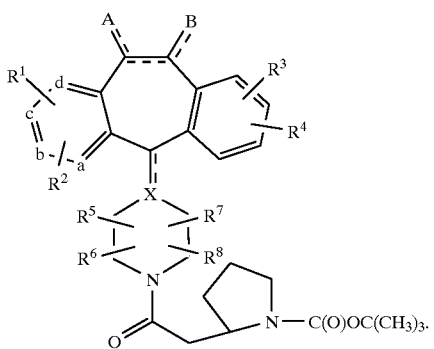

A compound of Formula 20.0 or 20.1 is then reacted with TFA followed by NaOH to produce a compound of Formula 21.0 or 21.1, respectively:

(21.0)

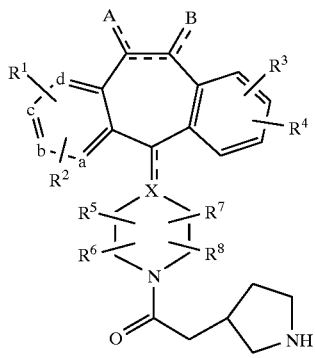

(21.1)

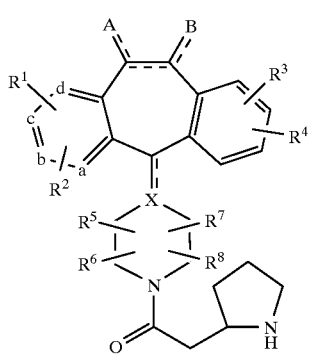

1-N-t-butoxycarbonylpyrrolidinyl acetic acid is prepared according to the procedure described in *J. Med. Chem.*, 33(1990), p. 71–77, by reacting homo-B-proline with di-tert-butyl dicarbonate at pH 9. Using (R)-(−)- or (S)-(+)-homo-B-proline produces the corresponding (R)-(−) or (S)-(+) t-butoxy compound, which in turn will produce the corresponding (R)-(−) or (S)-(+) compound of Formula 1.0. N-Boc-homoproline, prepared according to the procedure described in *Helvita Chimica Acta*, 59, (1976), p. 1918, produces the (S) isomer of the compound of Formula 21.1.

Compounds of Formula 19.0 can be prepared according to the procedures disclosed in WO 95/10516 published Apr. 20, 1995 and application Ser. No. 08/577,951 filed Dec. 22, 1995, and Ser. No. 08/615,760, filed Mar. 13, 1996, the disclosures of which have already been incorporated herein by reference thereto.

For example, preparation of the compounds:

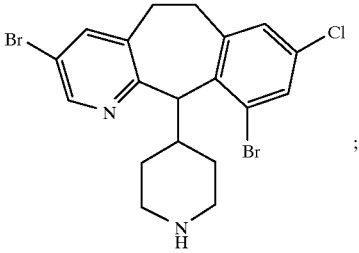

;

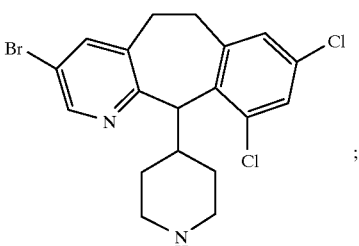

;

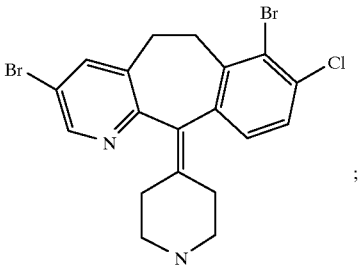

;

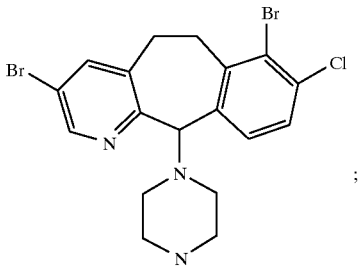

;

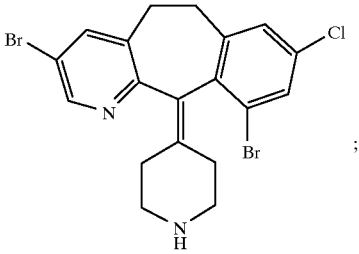

;

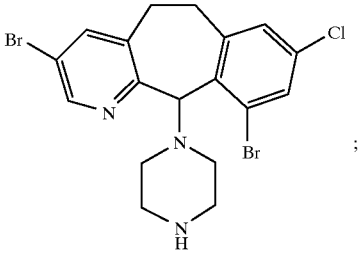

; and

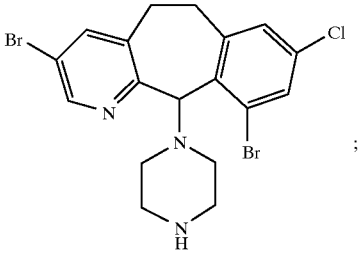

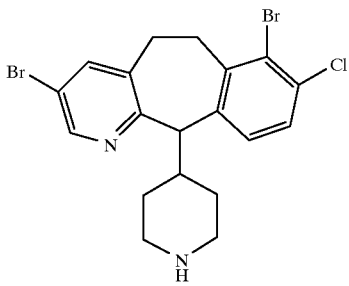

are disclosed in Preparative Example 8, Example 18, and Preparative Examples 4, 6, 7, 9 and 10, respectively, of application Ser. No. 08/615,760. These intermediate compounds, representative of the compounds of Formula 19.0, can be reacted with 1-N-t-butoxycarbonylpyrrolidinyl acetic acid or N-boc-homoproline to prepare the respective compounds of Formulas 21.0.

Compounds of formula (19.0) are also prepared as disclosed in U.S. Pat. No. 5,151,423 and acccording to methods described below. Compounds of formula (19.0) wherein the C-3 postion of the pyridine ring in the tricyclic structure is substituted by bromo and $R^3$ and $R^4$ are independently selected from hydrogen and halo can also be prepared by a procedure comprising the following steps:

(a) reacting an amide of the formula

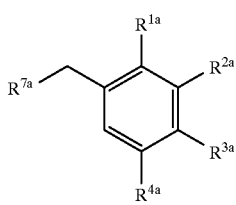

wherein $R^{11a}$ is Br, $R^{5a}$ is hydrogen and $R^{6a}$ is $C_1$–$C_6$ alkyl, aryl or heteroaryl; $R^{5a}$ is $C_1$–$C_6$ alkyl, aryl or heteroaryl and $R^{6a}$ is hydrogen; $R^{5a}$ and $R^{6a}$ are independently selected from the group consisting of $C_1$–$C_6$ alkyl and aryl; or $R^{5a}$ and $R^{6a}$, together with the nitrogen to which they are attached, form a ring comprising 4 to 6 carbon atoms or comprising 3 to 5 carbon atoms and one hetero moiety selected from the group consisting of —O— and —$NR^{9a}$—, wherein $R^{9a}$ is H, $C_1$–$C_6$ alkyl or phenyl; with a compound of the formula

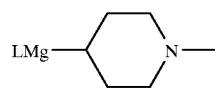

wherein $R^{1a}$, $R^{2a}$, $R^{3a}$ and $R^{4a}$ are are independently selected from the group consisting of hydrogen and halo and $R^{7a}$ is Cl or Br, in the presence of a strong base to obtain a compound of the formula

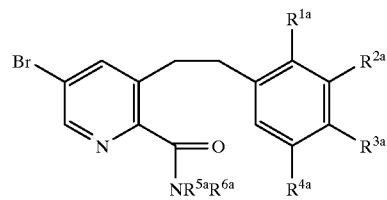

(b) reacting a compound of step (a) with (i) POCl$_3$ to obtain a cyano compound of the formula

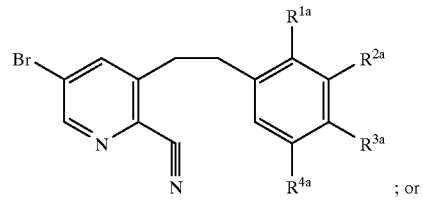

; or (ii) DIBALH to obtain an aldhyde of the formula

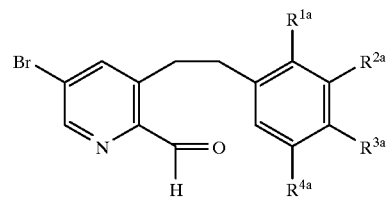

(c) reacting the cyano compound or the aldehyde with a piperidine derivative of the formula ![LMg-piperidine-N—]

wherein L is a leaving group selected from the group consisting of Cl and Br, to obtain a ketone or an alcohol of the formula below, respectively:

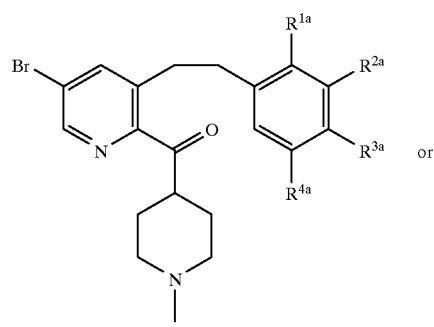 or

-continued

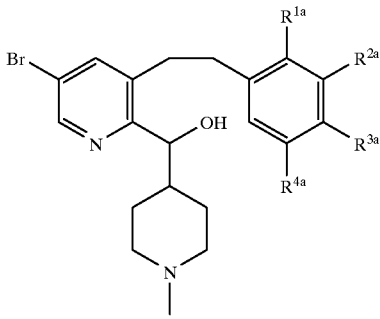

(d) (i) cyclizing the ketone with $CF_3SO_3H$ to obtain a compound of formula (19.0) wherein the dotted line represents a double bond; or (d) (ii) cyclizing the alcohol with polyphosphoric acid to obtain a compound of formula (19.0) wherein the dotted line represents a single bond.

Methods for preparing compounds of formula (19.0) disclosed in WO 95/10516, U.S. Pat. No. 5,151,423 and described below employ a tricyclic ketone intermediate. Such intermediates of the formula

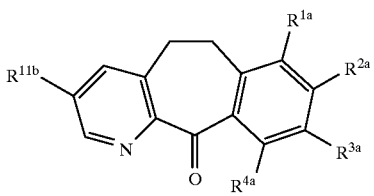

wherein $R^{11b}$, $R^{1a}$, $R^2a$, $R^3a$ and $R^4a$ are independently selected from the group consisting of hydrogen and halo, can be prepared by the following process comprising (a) reacting a compound of the formula

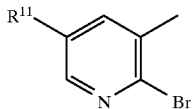

(i) with an amine of the formula $NHR^{5a}R^{6a}$, wherein $R^{5a}$ and $R^{6a}$ are as defined in the process above; in the presence of a palladium catalyst and carbon monoxide to obtain an amide of the formula:

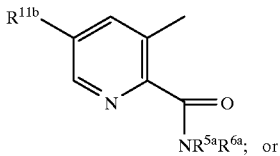

(ii) with an alcohol of the formula $R^{10a}OH$, wherein $R^{10a}$ is $C_1$–$C_6$ lower alkyl or $C_3$–$C_6$ cycloalkyl, in the presence of a palladium catalyst and carbon monoxide to obtain the ester of the formula

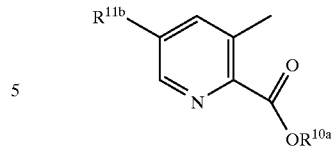

followed by reacting the ester with an amine of formula $NHR^{5a}R^{6a}$ to obtain the amide;

(b) reacting the amide with an iodo-substituted benzyl compound of the formula

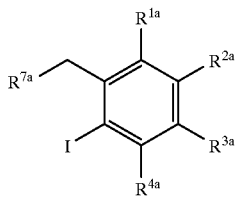

wherein $R^{1a}$, $R^{2a}$, $R^{3a}$, $R^{4a}$ and $R^{7a}$ are as defined above, in the presence of a strong base to obtain a compound of the formula

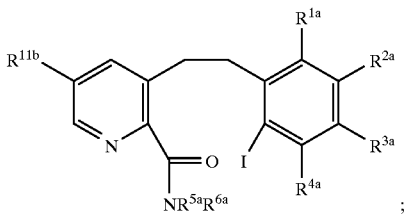

(c) cyclizing a compound of step (b) with a reagent of the formula $R^{8a}MgL$, wherein $R^{8a}$ is $C_1$–$C_8$ alkyl, aryl or heteroaryl and L is Br or Cl, provided that prior to cyclization, compounds wherein $R^{5a}$ or $R^{6a}$ is hydrogen are reacted with a suitable N-protecting group.

(+)-Isomers of compounds of formula (19.0) wherein X is C and the double bond is present can be prepared with high enantioselectivity by using a process comprising enzyme catalyzed transesterification. Preferably, a racemic compound of formula (19.0), wherein X is C and the double bond is present, is reacted with an enzyme such as Toyobo LIP-300 and an acylating agent such as trifluoroethly isobutyrate; the resultant (+)-amide is then hydrolyzed, for example by refluxing with an acid such as $H_2SO_4$, to obtain the corresponding optically enriched (+)-isomer. The double bond can then be reduced by methods well known in the art, e.g., by using DIBAL. Alternatively, a racemic compound of formula (19.0) wherein X is CH and the double bond is not present, can be prepared by first reducing a compound of formula (19.0) wherein X is C and the double bond is present, to the corresponding racemic compound of formula (19.0) wherein X is CH and then treating with the enzyme (Toyobo LIP-300) and acylating agent as described above to obtain the (+)-amide, which is hydrolyzed to obtain the optically enriched (+)-isomer. In a preferred enzymatic process, the C-10 substituent is not hydrogen.

Compounds of formula (1.0) comprising a pyridyl N-oxide in the tricyclic portion of the molecule can be prepared by procedures well known in the art. For example, the compound of formula (19.0) can be reacted with MCPBA in a suitable organic solvent, e.g., $CH_2Cl_2$ (usually anhydrous), at a suitable temperature, to obtain an N-oxide of formula (19.1)

(19.1)

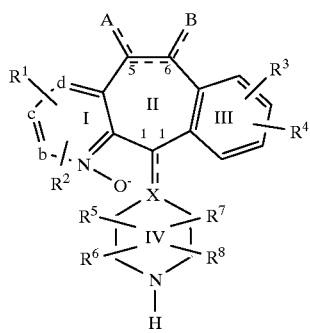

Generally, the organic solvent solution of formula (19.0) is cooled to about 0° C. before the MCPBA is added. The reaction is then allowed to warm to room temperature during the reaction period. The desired product can be recovered by standard separation means, for example, the reaction mixture can be washed with an aqueous solution of a suitable base, e.g., saturated $NaHCO_3$ or NaOH (e.g., i N NaOH), and then dried over anhydrous $MgSO_4$. The solution containing the product can be concentrated in vacuo, and the product can be purified by standard means, e.g., by chromatography using silica gel (e.g., flash column chromatography).

To produce the compounds of Formula 1.0, compounds of Formula 21 are reacted with reagents appropriate for attaching the various R groups as exemplified below. Those skilled in the art will appreciate that the methods of preparing of compounds of Formula 1.0 are not limited to the following examples, but that other procedures known in the art may also be applicable.

Following are typical examples of the preparation of various starting materials, including (R)-(−) and (S)-(+) 1-N-t-butoxycarbonylpyrrolidinyl-3-acetic acid, and of compounds of formula I.

PREPARATIVE EXAMPLE 1

(R)-(−) 1-N-t-butoxycarbonylpyrrolidinyl-3-acetic acid

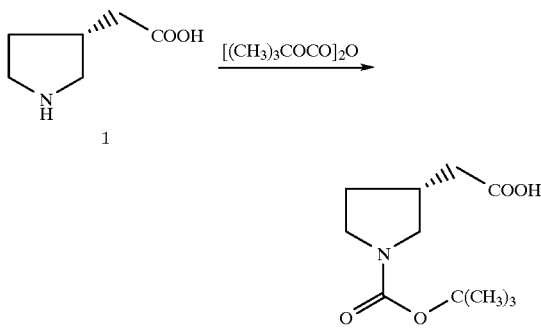

Suspend 3.8 g (29.43 mmol) of (R)-homo-b-proline 1 in 75 mL of $CH_3OH$—$H_2O$ (1:1). Adjust to pH with 1 N NaOH. Add 7.06 g (32.34 mmol) di-tert-butyl dicarbonate slowly (25 min) while maintaining at pH 9 and stir the mixture at room temperature overnight. Concentrate the mixture in vacuo to a residue, then partition the residue between 100 mL $CH_2Cl_2$ and 100 mL of 10% citric acid (aqueous). Dry the organic phase over $MgSO_4$ and concentrate in in vacuo to give 2.1 g of compound 3, m. p.=100° C.; Mas Spec.: $MH^+$=230.

PREPARATIVE EXAMPLE 2

(S)-(+) 1-N-t-butoxycarbonylpyrrolidinyl-3-acetic

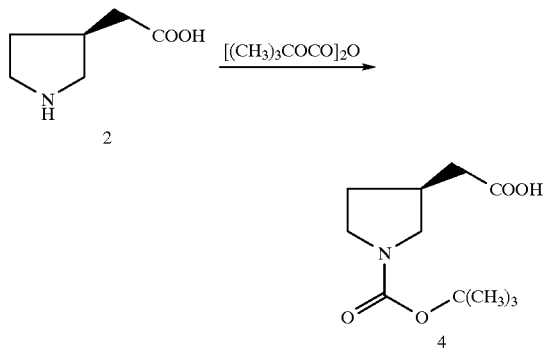

React 1.9 g (1.47 mmol) of (S)-homo-b-proline 2 with 3.53 g (1.61 mmol) of di-tert-butyl dicarbonate using substantially the same procedure as described above to give 2.8 g of compound 4, m.p.=102° C.; $MH^+$=230; $^1H$ NMR ($CDCl_3$, 200 MHz): 3.2–3.7 (m, 3H); 2.9 (m,1H); 2.4–2.6 (m, 3H); 2.1 (m, 2H); 1.55 (m, 1H); 1.4 (s, 9H).

PREPARATIVE EXAMPLE 3

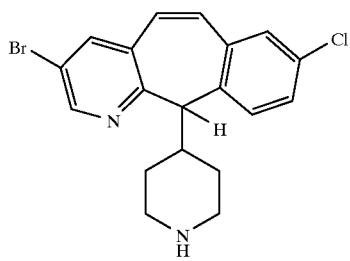

Step A:

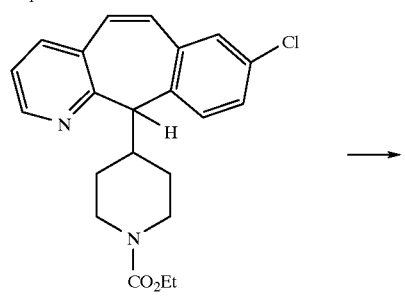

-continued

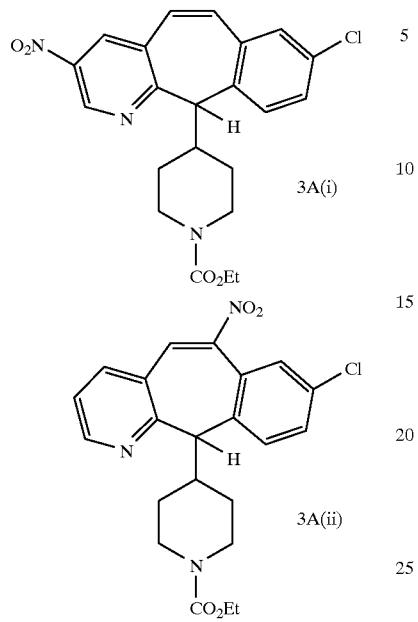

Combine 14.95 g (39 mmol) of 8-chloro-11-(1-ethoxy-carbonyl-4-piperidinyl)-11H-benzo[5,6]cyclohepta[1,2-b]pyridine and 150 mL of $CH_2Cl_2$, then add 13.07 g (42.9 mmol) of $(nBu)_4NNO_3$ and cool the mixture to 0° C. Slowly add (dropwise) a solution of 6.09 mL (42.9 mmol) of TFAA in 20 mL of $CH_2Cl_2$ over 1.5 hours. Keep the mixture at 0° C. overnight, then wash successively with saturated $NaHCO_3$ (aqueous), water and brine. Dry the organic solution over $Na_2SO_4$, concentrate in vacuo to a residue and chromatograph the residue (silica gel, EtOAc/hexane gradient) to give 4.32 g and 1.90 g of the two product compounds 3A(i) and 3A(ii), respectively.

Mass Spec. for compound 3A(i): $MH^+$=428.2;

Mass Spec. for compound 3A(ii): $MH^+$=428.3

Step B:

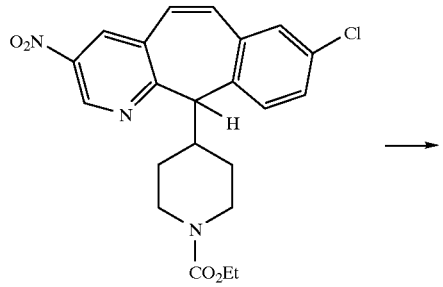

-continued

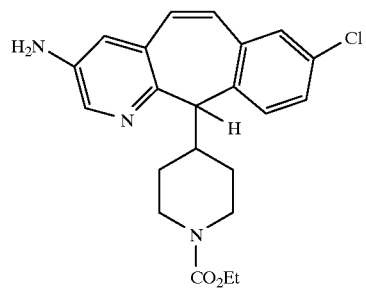

Combine 22.0 g (51.4 mmol) of the product 3A(i) from Step A, 150 mL of 85% EtOH (aqueous), 25.85 g (0.463 mole) of Fe powder and 2.42 g (21.8 mmol) of $CaCl_2$, and heat at reflux overnight. Add 12.4 g (0.222 mole) of Fe powder and 1.2 g (10.8 mmol) of $CaCl_2$ and heat at reflux for 2 hours. Add another 12.4 g (0.222 mole) of Fe powder and 1.2 g (10.8 mmol) of $CaCl_2$ and heat at reflux for 2 hours more. Filter the hot mixture through celite®, wash the celite® with 50 mL of hot EtOH and concentrate the filtrate in vacuo to a residue. Add 100 mL of anhydrous EtOH, concentrate to a residue and chromatograph the residue (silica gel, $MeOH/CH_2Cl_2$ gradient) to give 16.47 g of the product compound.

Step C:

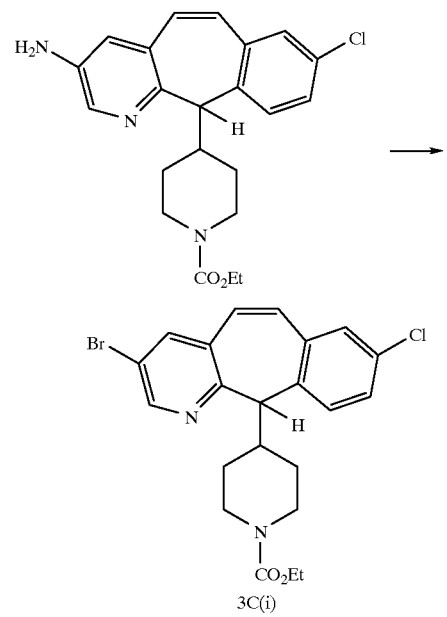

-continued

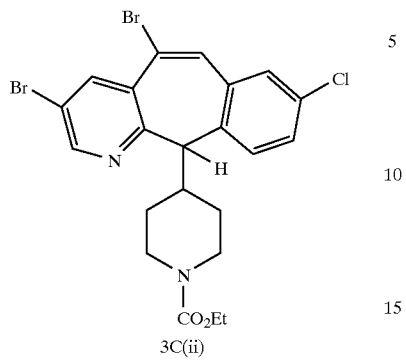

3C(ii)

Combine 16.47 g (41.4 mmol) of the product from Step B, and 150 mL of 48% HBr (aqueous) and cool to −3° C. Slowly add (dropwise) 18 mL of bromine, then slowly add (dropwise) a solution of 8.55 g (0.124 mole) of $NaNO_2$ in 85 mL of water. Stir for 45 minutes at −3° to 0° C., then adjust to pH=10 by adding 50% NaOH (aqueous). Extract with EtOAc, wash the extracts with brine and dry the extracts over $Na_2SO_4$. Concentrate to a residue and chromatograph (silica gel, EtOAc/hexane gradient) to give 10.6 g and 3.28 g of the two product compounds 3C(i) and 3C(ii), respectively.

Mass Spec. for compound 3C(i): $MH^+$=461.2;
Mass Spec. for compound 3C(ii): $MH^+$=539

Step D:

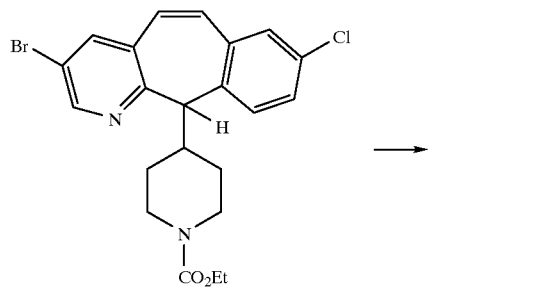

Hydrolyze the product 3C(i) of Step C by dissolving in concentrated HCl and heating to about 100° C. for @ 16 hours. Cool the mixture, the neutralize with 1 M NaOH (aqueous). Extract with $CH_2Cl_2$, dry the extracts over $MgSO_4$, filter and concentrate in vacuo to the title compound. Mass Spec.: $MH^+$=466.9

PREPARATIVE EXAMPLE 4

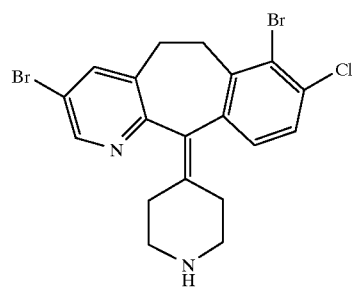

Step A:

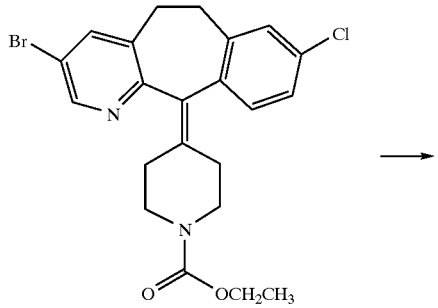

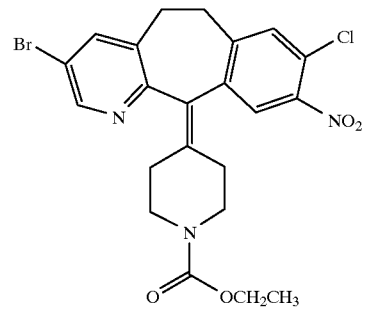

Combine 25.86 g (55.9 mmol) of 4-(8-chloro-3-bromo-5,6-dihydro-11H-benzo[5,6]cyclohepta[1,2-b]pyridin-11-ylidene)-1-piperidine-1-carboxylic acid ethyl ester and 250 mL of concentrated $H_2SO_4$ at −5° C., then add 4.8 g (56.4 mmol) of $NaNO_3$ and stir for 2 hours. Pour the mixture into 600 g of ice and basify with concentrated $NH_4OH$ (aqueous). Filter the mixture, wash with 300 mL of water, then extract with 500 mL of $CH_2Cl_2$. Wash the extract with 200 mL of water, dry over $MgSO_4$, then filter and concentrate in vacuo to a residue. Chromatograph the residue (silica gel, 10% EtOAc/$CH_2Cl_2$) to give 24.4 g (86% yield) of the product. m.p.=165–167° C., Mass Spec.: $MH^+$=506, 508 (Cl).

elemental analysis: calculated—C, 52.13; H, 4.17; N, 8.29, found—C, 52.18; H, 4.51; N, 8.16

Step B:

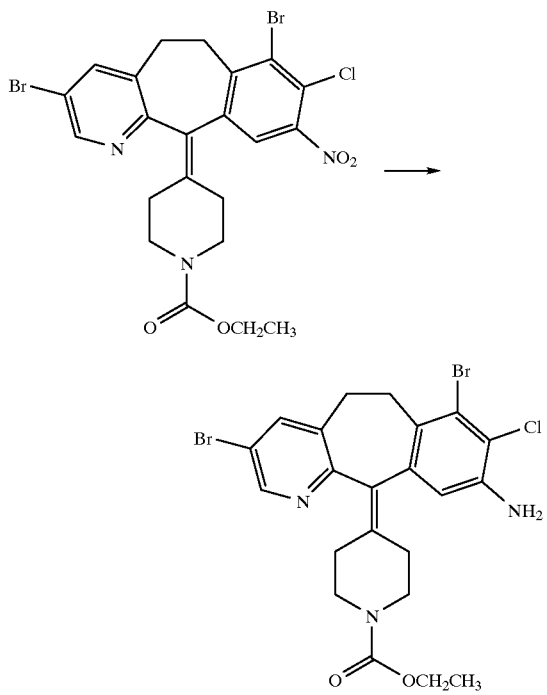

Combine 20 g (40.5 mmol) of the product of Step A and 200 mL of concentrated H₂SO₄ at 20° C., then cool the mixture to 0° C. Add 7.12 g (24.89 mmol) of 1,3-dibromo-5,5-dimethyl-hydantoin to the mixture and stir for 3 hours at 20° C. Cool to 0° C., add an additional 1.0 g (3.5 mmol) of the dibromohydantoin and stir at 20° C. for 2 hours. Pour the mixture into 400 g of ice, basify with concentrated NH₄OH (aqueous) at 0° C., and collect the resulting solid by filtration. Wash the solid with 300 mL of water, slurry in 200 mL of acetone and filter to provide 19.79 g (85.6% yield) of the product. m.p.=236–237° C., Mass Spec.: MH⁺=586 (Cl).

elemental analysis: calculated—C, 45.11; H, 3.44; N, 7.17, found—C, 44.95; H, 3.57; N, 7.16

Step C:

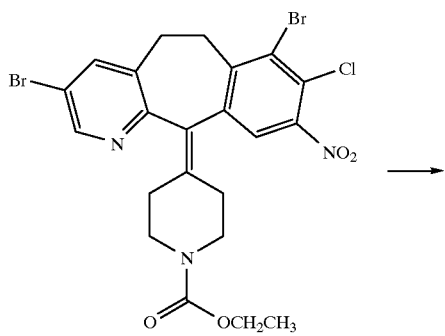

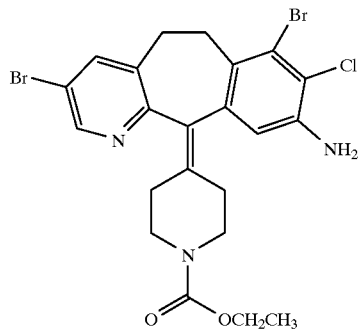

Combine 25 g (447 mmol) of Fe filings, 10 g (90 mmol) of CaCl₂ and a suspension of 20 g (34.19 mmol) of the product of Step B in 700 mL of 90:10 EtOH/water at 50° C. Heat the mixture at reflux overnight, filter through Celite® and wash the filter cake with 2×200 mL of hot EtOH. Combine the filtrate and washes, and concentrate in vacuo to a residue. Extract the residue with 600 mL of CH₂Cl₂, wash with 300 mL of water and dry over MgSO₄. Filter and concentrate in vacuo to a residue, then chromatograph (silica gel, 30% EtOAc/CH₂Cl₂) to give 11.4 g (60% yield) of the product. m.p.=211–212° C., Mass Spec.: MH⁺=556 (Cl).

elemental analysis: calculated—C, 47.55; H, 3.99; N, 7.56, found—C, 47.45; H, 4.31; N, 7.49

Step D:

Slowly add (in portions) 20 g (35.9 mmol) of the product of Step C to a solution of 8 g (116 mmol) of NaNO₂ in 120 mL of concentrated HCl (aqueous) at −10° C. Stir the resulting mixture at 0° C. for 2 hours, then slowly add (dropwise) 150 mL (1.44 mole) of 50% H₃PO₂ at 0° C. over a 1 hour period. Stir at 0° C. for 3 hours, then pour into 600 g of ice and basify with concentrated NH₄OH (aqueous). Extract with 2×300 mL of CH₂Cl₂, dry the extracts over MgSO₄, then filter and concentrate in vacuo to a residue. Chromatograph the residue (silica gel, 25% EtOAc/hexanes) to give 13.67 g (70% yield) of the product. m.p.=163–165° C., Mass Spec.: MH⁺=541 (Cl).

elemental analysis: calculated—C, 48.97; H, 4.05; N, 5.22, found—C, 48.86; H, 3.91; N, 5.18

Step E:

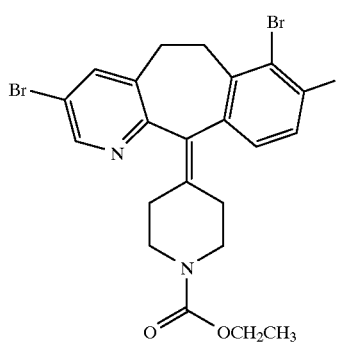

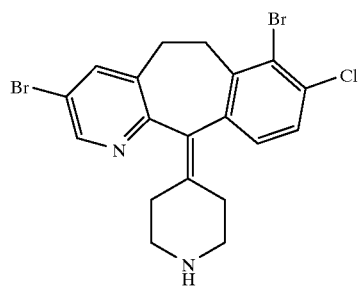

Combine 6.8 g (12.59 mmol) of the product of Step D and 100 mL of concentrated HCl (aqueous) and stir at 85° C. overnight. Cool the mixture, pour it into 300 g of ice and basify with concentrated NH₄OH (aqueous). Extract with 2×300 mL of CH₂Cl₂, then dry the extracts over MgSO₄. Filter, concentrate in vacuo to a residue, then chromatograph (silica gel, 10% MeOH/EtOAc+2% NH₄OH (aq.)) to give 5.4 g (92% yield) of the title compound. m.p.=172–174° C., Mass Spec.: MH⁺=469 (FAB).

elemental analysis: calculated—C, 48.69; H, 3.65; N, 5.97. found—C, 48.83; H, 3.80; N, 5.97

PREPARATIVE EXAMPLE 5

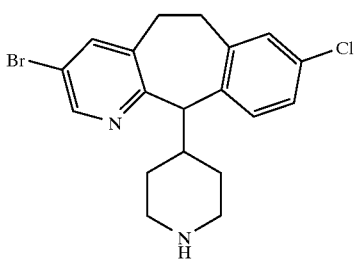

Step A:

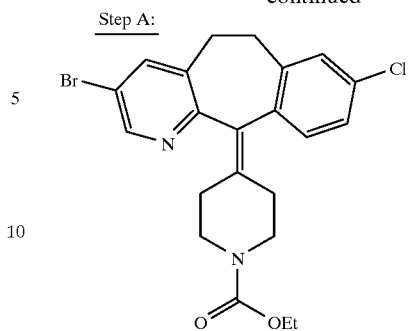

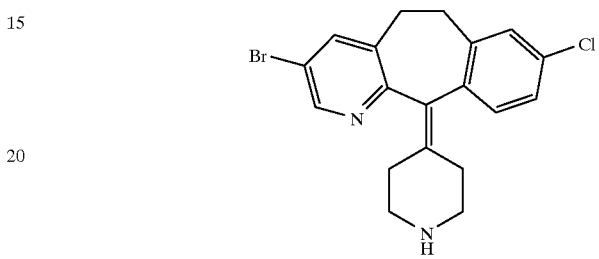

Hydrolyze 2.42 g of 4-(8-chloro-3-bromo-5,6-dihydro-11H-benzo[5,6]cyclohepta[1,2-b]pyridin-11-ylidene)-1-piperidine-1-carboxylic acid ethyl ester via substantially the same procedure as described in Preparative Example 3, Step D, to give 1.39 g (69% yield) of the product.

Step B:

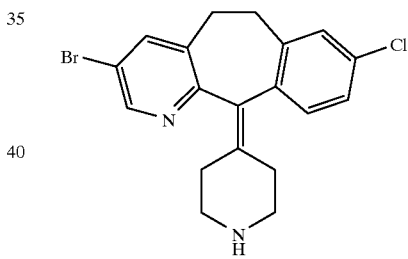

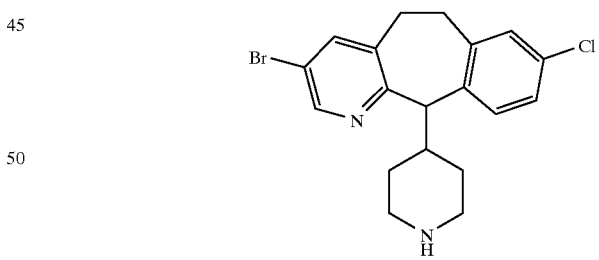

Combine 1 g (2.48 mmol) of the product of Step A and 25 mL of dry toluene, add 2.5 mL of 1 M DIBAL in toluene and heat the mixture at reflux. After 0.5 hours, add another 2.5 mL of 1 M DIBAL in toluene and heat at reflux for 1 hour. (The reaction is monitored by TLC using 50% MeOH/CH₂Cl₂+NH₄OH (aqueous).) Cool the mixture to room temperature, add 50 mL of 1 N HCl (aqueous) and stir for 5 min. Add 100 mL of 1 N NaOH (aqueous), then extract with EtOAc (3×150 mL). Dry the extracts over MgSO₄, filter and concentrate in vacuo to give 1.1 g of the title compound.

PREPARATIVE EXAMPLE 6

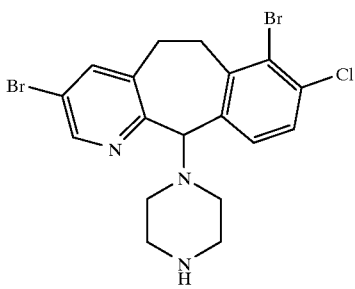

[racemic as well as (+)- and (−)-isomers]

Step A:

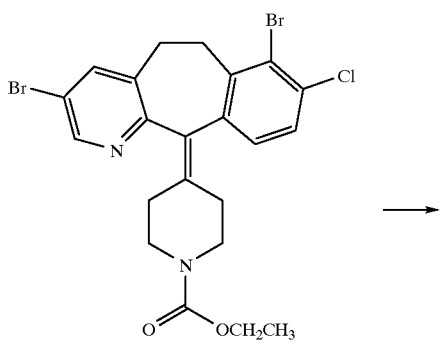

Combine 16.6 g (0.03 mole) of the product of Preparative Example 4, Step D, with a 3:1 solution of CH$_3$CN and water (212.65 mL CH$_3$CN and 70.8 mL of water) and stir the resulting slurry overnight at room temperature. Add 32.833 g (0.153 mole) of NaIO$_4$ and then 0.31 g (2.30 mmol) of RuO$_2$ and stir at room temperature give 1.39 g (69% yield) of the product. (The addition of RuO is accompanied by an exothermic reaction and the temperature climbs from 20° to 30° C.) Stir the mixture for 1.3 hrs. (temperature returned to 25° C. after about 30 min.), then filter to remove the solids and wash the solids with CH$_2$Cl$_2$. Concentrate the filtrate in vacuo to a residue and dissolve the residue in CH$_2$Cl$_2$. Filter to remove insoluble solids and wash the solids with CH$_2$Cl$_2$. Wash the filtrate with water, concentrate to a volume of about 200 mL and wash with bleach, then with water. Extract with 6 N HCl (aqueous). Cool the aqueous extract to 0° C. and slowly add 50% NaOH (aqueous) to adjust to pH=4 while keeping the temperature <30° C. Extract twice with CH$_2$Cl$_2$, dry over MgSO$_4$ and concentrate in vacuo to a residue. Slurry the residue in 20 mL of EtOH and cool to 0° C. Collect the resulting solids by filtration and dry the solids in vacuo to give 7.95 g of the product. $^1$H NMR (CDCl$_3$, 200 MHz): 8.7 (s, 1H); 7.85 (m, 6H); 7.5 (d, 2H); 3.45 (m, 2H); 3.15 (m, 2H).

Step B:

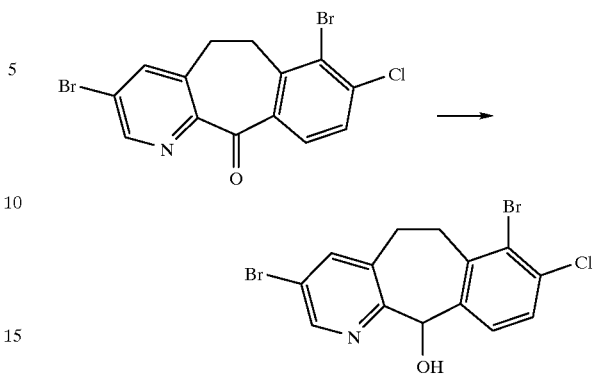

Combine 21.58 g (53.75 mmol) of the product of Step A and 500 mL of an anhydrous 1:1 mixture of EtOH and toluene, add 1.43 g (37.8 mmol) of NaBH$_4$ and heat the mixture at reflux for 10 min. Cool the mixture to 0° C., add 100 mL of water, then adjust to pH=4–5 with 1 M HCl (aqueous) while keeping the temperature <1 0C. Add 250 mL of EtOAc and separate the layers. Wash the organic layer with brine (3×50 mL) then dry over Na$_2$SO$_4$. Concentrate in vacuo to a residue (24.01 g) and chromatograph the residue (silica gel, 30% hexane/CH$_2$Cl$_2$) to give the product. Impure fractions were purified by rechromatography. A total of 18.57 g of the product was obtained. $^1$H NMR (DMSO-d$_6$, 400 MHz): 8.5 (s, 1H); 7.9 (s, 1H); 7.5 (d of d, 2H); 6.2 (s, 1H); 6.1 (s, 1H); 3.5 (m, 1H); 3.4 (m, 1H); 3.2 (m, 2H).

Step C:

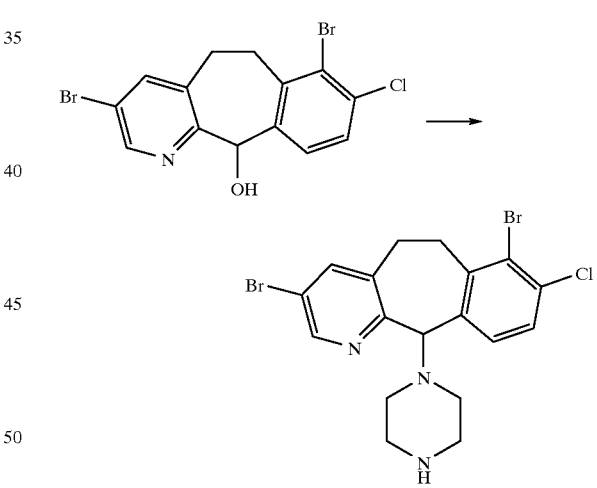

Combine 18.57 g (46.02 mmol) of the product of Step B and 500 mL of CHCl$_3$, then add 6.70 mL (91.2 mmol) of SOCl$_2$, and stir the mixture at room temperature for 4 hrs. Add a solution of 35.6 g (0.413 mole) of piperazine in 800 mL of THF over a period of 5 min. and stir the mixture for 1 hr. at room temperature. Heat the mixture at reflux overnight, then cool to room temperature and dilute the mixture with 1 L of CH$_2$Cl$_2$. Wash with water (5×200 mL), and extract the aqueous wash with CHCl$_3$ (3×100 mL). Combine all of the organic solutions, wash with brine (3×200 mL) and dry over MgSO$_4$. Concentrate in vacuo to a residue and chromatograph (silica gel, gradient of 5%, 7.5%, 10% MeOH/CH$_2$Cl$_2$+NH$_4$OH) to give 18.49 9 of the title compound as a racemic mixture.

Step D—Separation of Enantiomers:

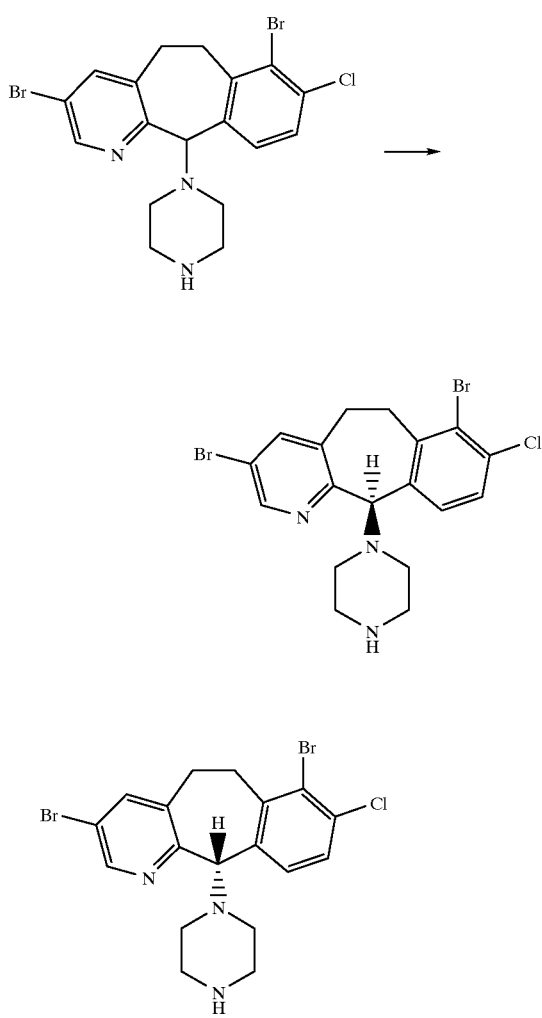

The racemic title compound of Step C is separated by preparative chiral chromatography (Chiralpack AD, 5 cm X 50 cm column, flow rate 100 mL/min., 20% iPrOH/hexane+ 0.2% diethylamine), to give 9.14 g of the (+)-isomer and 9.30 g of the (−)-isomer.

Physical chemical data for (+)-isomer: m.p.=74.5°–77.5° C.; Mass Spec. MH$^+$=471.9; $[a]_D^{25}$=+97.4° (8.48 mg/2 mL MeOH).

Physical chemical data for (−)-isomer: m.p.=82.9°–84.5° C.; Mass Spec. MH$^+$=471.8; $[a]_D^{25}$=−97.4° (8.32 mg/2 mL MeOH).

PREPARATIVE EXAMPLE 7

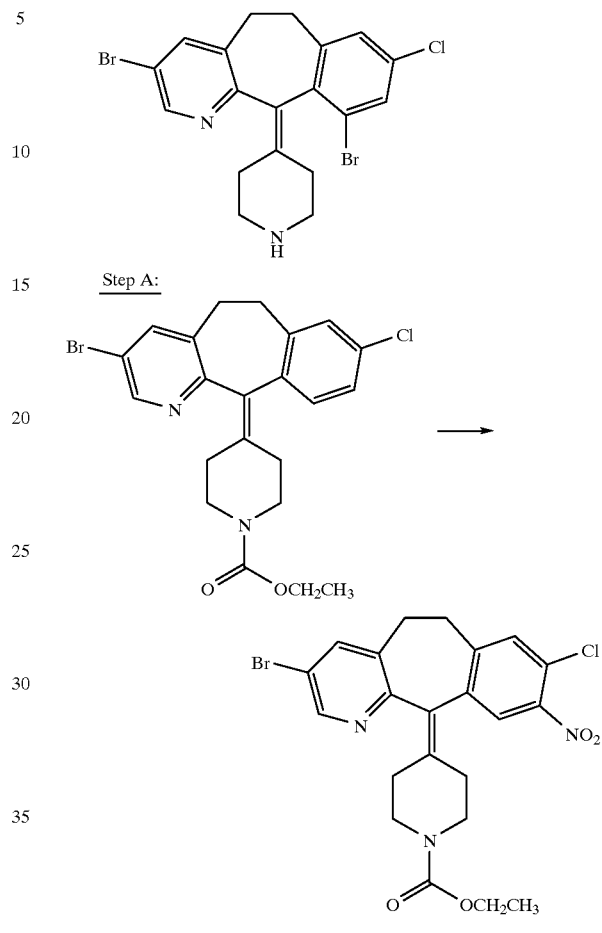

Step A:

Combine 15 g (38.5 mmol) of 4-(8-chloro-3-bromo-5,6-dihydro-11H-benzo[5,6]cyclohepta[1,2-b]pyridin-11-ylidene)-1-piperidine-1-carboxylic acid ethyl ester and 150 mL of conc. H$_2$SO$_4$ at −5° C., then add 3.89 g (38.5 mmol) of KNO$_3$ and stir for 4 h. Pour the mixture into 3 L of ice and basify with 50% NaOH (aqueous). Extract with CH$_2$Cl$_2$, dry over MgSO$_4$, then filter and concentrate in vacuo to a residue. Recrystallize the residue from acetone to give 6.69 g of the product. $^1$H NMR (CDCl$_3$, 200 MHz): 8.5 (s, 1H); 7.75 (s, 1H); 7.6 (s, 1H); 7.35 (s, 1H); 4.15 (q, 2H); 3.8 (m, 2H); 3.5–3.1 (m, 4H); 3.0–2.8 (m, 2H); 2.6–2.2 (m, 4H); 1.25 (t, 3H).

Step B:

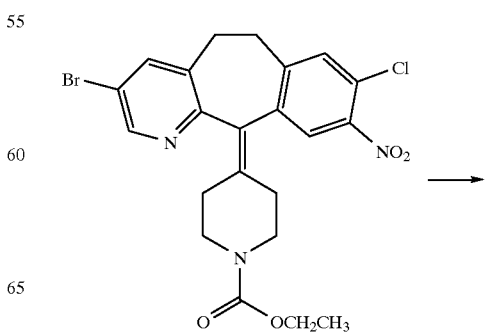

-continued

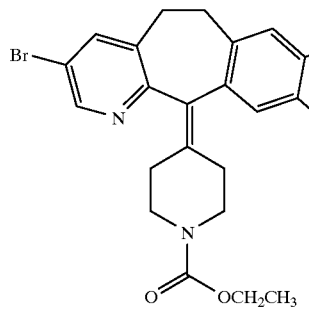

Combine 6.69 g (13.1 mmol) of the product of Step A and 100 mL of 85% EtOH/water, add 0.66 g (5.9 mmol) of CaCl$_2$ and 6.56 g (117.9 mmol) of Fe and heat the mixture at reflux overnight. Filter the hot reaction mixture through celite® and rinse the filter cake with hot EtOH. Concentrate the filtrate in vacuo to give 7.72 g of the product. Mass Spec.: MH$^+$=478.0

Step C:

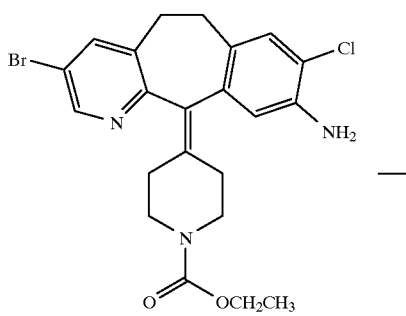

Combine 7.70 g of the product of Step B and 35 mL of HOAc, then add 45 mL of a solution of Br$_2$ in HOAc and stir the mixture at room temperature overnight. Add 300 mL of 1 N NaOH (aqueous), then 75 mL of 50% NaOH (aqueous) and extract with EtOAc. Dry the extract over MgSO$_4$ and concentrate in vacuo to a residue. Chromatograph the residue (silica gel, 20%–30% EtOAc/hexane) to give 3.47 g of the product (along with another 1.28 g of partially purified product). Mass Spec.: MH$^+$=555.9. $^1$H NMR (CDCl$_3$, 300 MHz): 8.5 (s, 1H); 7.5 (s, 1H); 7.15 (s, 1H); 4.5 (s, 2H); 4.15 (m, 3H); 3.8 (brs, 2H); 3.4–3.1 (m, 4H); 9–2.75 (m, 1H); 2.7–2.5 (m, 2H); 2.4–2.2 (m, 2H); 1.25 (m, 3H).

Step D:

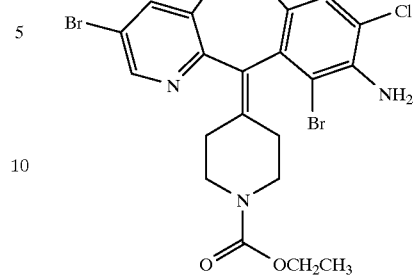

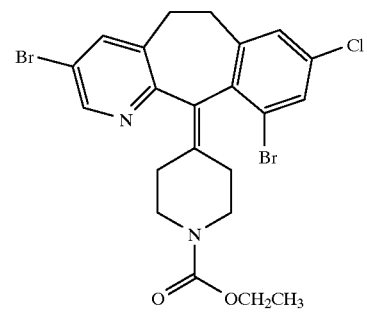

Combine 0.557 g (5.4 mmol) of t-butylnitrite and 3 mL of DMF, and heat the mixtre at to 60°–70° C. Slowly add (dropwise) a mixture of 2.00 g (3.6 mmol) of the product of Step C and 4 mL of DMF, then cool the mixture to room temperature. Add another 0.64 mL of t-butylnitrite at 40° C. and reheat the mixture to 60°–70° C. for 0.5 hrs. Cool to room temperature and pour the mixture into 150 mL of water. Extract with CH$_2$Cl$_2$, dry over MgSO$_4$ and concentrate in vacuo to a residue. Chromatograph the residue (silica gel, 10%–20% EtOAc/hexane) to give 0.74 g of the product. Mass Spec.: MH$^+$=541.0. $^1$H NMR (CDCl$_3$, 200 MHz): 8.52 (s, 1H); 7.5 (d, 2H); 7.2 (s, 1H); 4.15 (q, 2H); 3.9–3.7 (m, 2H); 3.5–3.1 (m, 4H); 3.0–2.5 (m, 2H); 2.4–2.2 (m, 2H); 2.1–1.9 (m, 2H); 1.26 (t, 3H).

Step E:

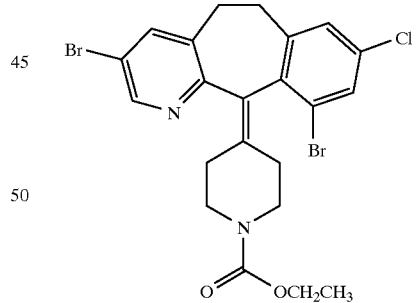

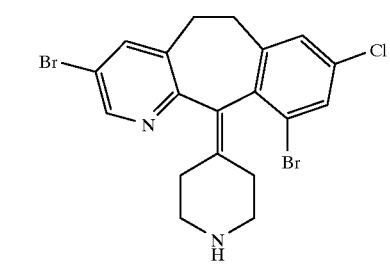

Combine 0.70 g (1.4 mmol) of the product of Step D and 8 mL of concentrated HCl (aqueous) and heat the mixture at reflux overnight. Add 30 mL of 1 N NaOH (aqueous), then 5 mL of 50% NaOH (aqueous) and extract with CH₂Cl₂. Dry the extract over MgSO₄ and concentrate in vacuo to give 0.59 g of the title compound. Mass Spec.: M⁺=468.7. m.p.=123.9°–124.2° C.

PREPARATIVE EXAMPLE 8

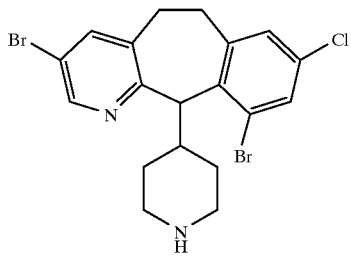

[racemic as well as (+)- and (–)-isomers]

Step A:

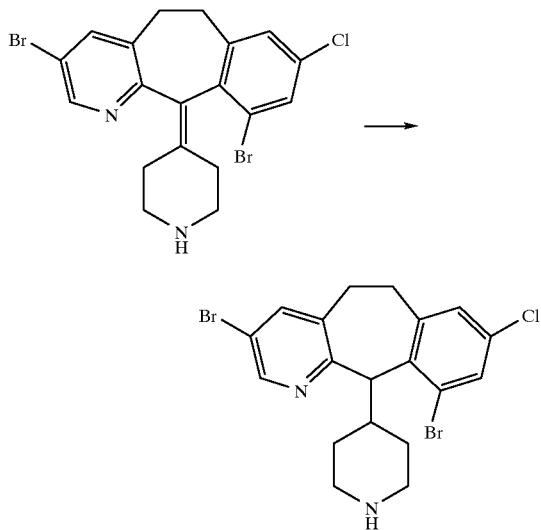

Prepare a solution of 8.1 g of the title compound from Preparative Example 7 in toluene and add 17.3 mL of a 1 M solution of DIBAL in toluene. Heat the mixture at reflux and slowly add (dropwise) another 21 mL of 1 M DIBAL/toluene solution over a period of 40 min. Cool the reaction mixture to about 0° C. and add 700 mL of 1 M HCl (aqueous). Separate and discard the organic phase. Wash the aqueous phase with CH₂Cl₂, discard the extract, then basify the aqueous phase by adding 50% NaOH (aqueous). Extract with CH₂Cl₂, dry the extract over MgSO₄ and concentrate in vacuo to give 7.30 g of the title compound, which is a racemic mixture of enantiomers.

Step B—Separation of Enantiomers:

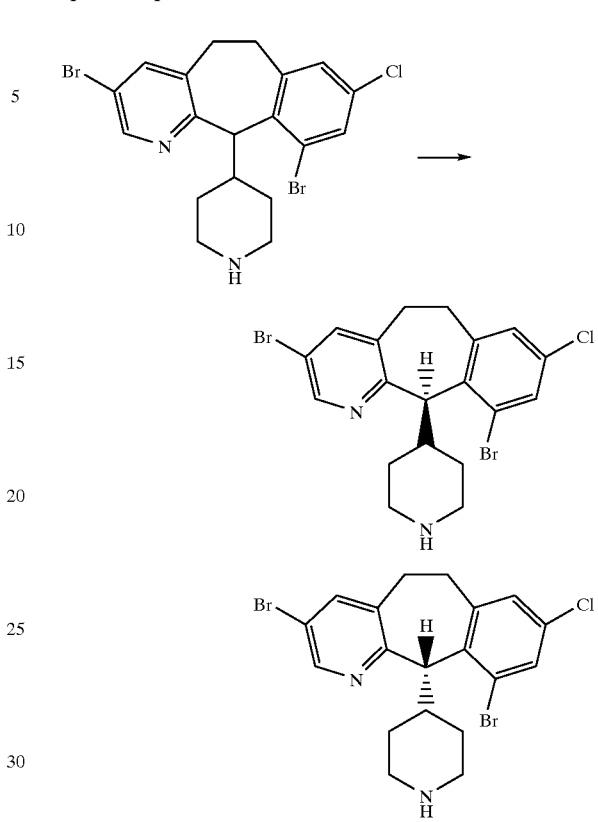

The racemic title compound of Step A is separated by preparative chiral chromatography (Chiralpack AD, 5 cm×50 cm column, using 20% iPrOH/hexane+0.2% diethylamine), to give the (+)-isomer and the (–)-isomer of the title compound.

Physical chemical data for (+)-isomer: m.p.=148.8° C.; Mass Spec. MH⁺=469; $[a]_D^{25}$+65.60 (mg/2 mL MeOH).

Physical chemical data for (–)-isomer: m.p.=112° C.; Mass Spec. MH⁺=469; $[a]_D^{25}$=–65.2° (mg/2 mL MeOH).

PREPARATIVE EXAMPLE 9

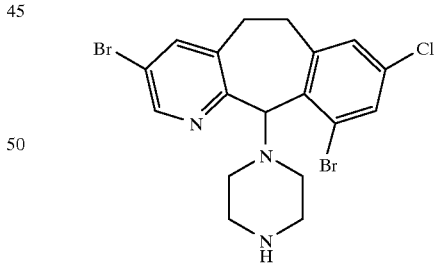

[racemic as well as (+)- and (–)-isomers]
Step A:

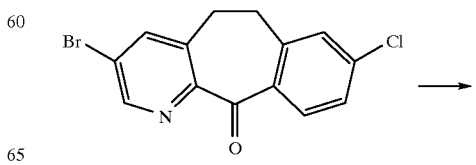

-continued

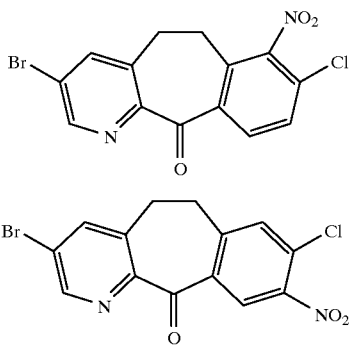

Combine 40.0 g (0.124 mole) of the starting ketone and 200 mL of H₂SO₄ and cool to 0° C. Slowly add 13.78 g (0.136 mole) of KNO₃ over a period of 1.5 hrs., then warm to room temperature and stir overnight. Work up the reaction using substantially the same procedure as described for Preparative Example 4, Step A. Chromatograph (silica gel, 20%, 30%, 40%, 50% EtOAc/hexane, then 100% EtOAc) to give 28 g of the 9-nitro product, along with a smaller quantity of the 7-nitro product and 19 g of a mixture of the 7-nitro and 9-nitro compounds.

Step B:

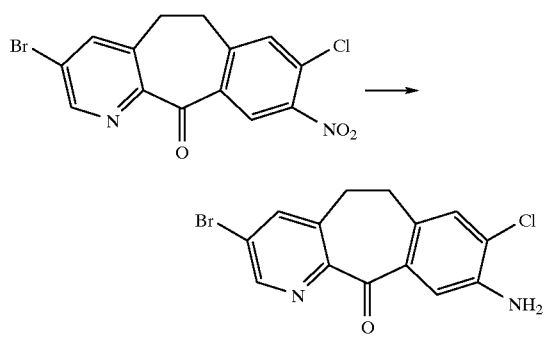

React 28 g (76.2 mmol) of the 9-nitro product of Step A, 400 mL of 85% EtOH/water, 3.8 g (34.3 mmol) of CaCl₂ and 38.28 g (0.685 mole) of Fe using substantially the same procedure as described for Preparative Example 4, Step C, to give 24 g of the product Step C:

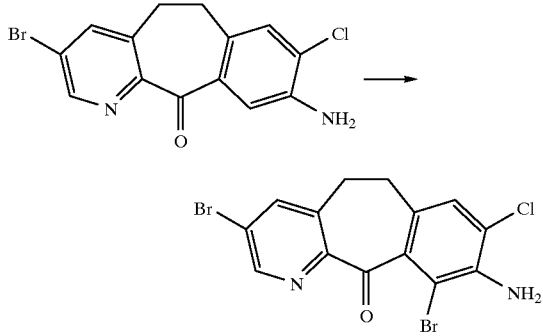

Combine 13 g (38.5 mmol) of the product of Step B, 140 mL of HOAc and slowly add a solution of 2.95 mL (57.8 mmol) of Br₂ in 10 mL of HOAc over a period of 20 min. Stir the reaction mixture at room temperature, then concentrate in vacuo to a residue. Add CH₂Cl₂ and water, then adjust to pH=8–9 with 50% NaOH (aqueous). Wash the organic phase with water, then brine and dry over Na₂SO₄. Concentrate in vacuo to give 11.3 g of the product.

Step D:

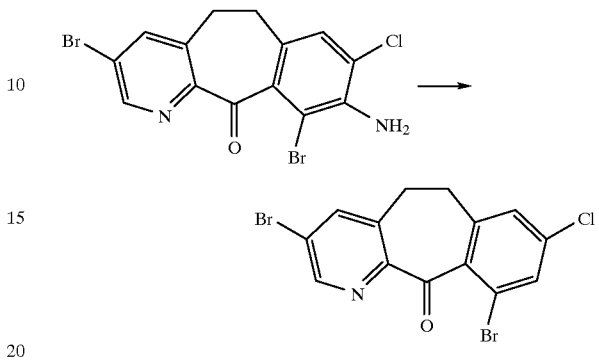

Cool 100 mL of concentrated HCl (aqueous) to 0° C., then add 5.61 g (81.4 mmol) of NaNO₂ and stir for 10 min. Slowly add (in portions) 11.3 g (27.1 mmol) of the product of Step C and stir the mixture at 0°–3° C. for 2.25 hrs. Slowly add (dropwise) 180 mL of 50% H₃PO₂ (aqueous) and allow the mixture to stand at 0° C. overnight. Slowly add (dropwise) 150 mL of 50% NaOH over 30 min., to adjust to pH=9, then extract with CH₂Cl₂. Wash the extract with water, then brine and dry over Na₂SO₄. Concentrate in vacuo to a residue and chromatograph (silica gel, 2% EtOAc/CH₂Cl₂) to give 8.6 g of the product.

Step E:

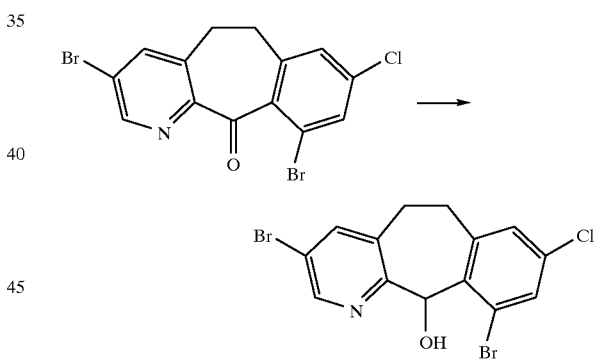

Combine 8.6 g (21.4 mmol) of the product of Step D and 300 mL of MeOH and cool to 0°–2° C. Add 1.21 g (32.1 mmol) of NaBH₄ and stir at ~0° C. for 1 hr. Add another 0.121 g (3.21 mmol) of NaBH₄, stir for 2 hr. at 0° C., then let stand overnight at 0° C. Concentrate in vacuo to a residue then partition the residue between CH₂Cl₂ and water. Separate the organic phase and concentrate in vacuo (50° C.) to give 8.2 g of the product.

Step F:

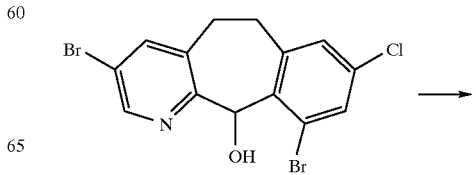

-continued

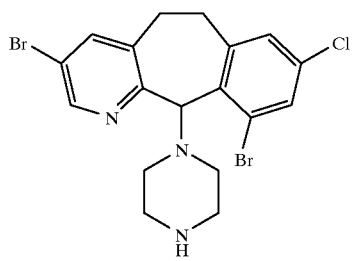

Combine 8.2 g (20.3 mmol) of the product of Step E and 160 mL of $CH_2Cl_2$, cool to 0° C., then slowly add (dropwise) 14.8 mL (203 mmol) of $SOCl_2$ over a 30 min. period. Warm the mixture to room temperature and stir for 4.5 hrs., then concentrate in vacuo to a residue, add $CH_2Cl_2$ and wash with 1 N NaOH (aqueous) then brine and dry over $Na_2SO_4$. Concentrate in vacuo to a residue, then add dry THF and 8.7 g (101 mmol) of piperazine and stir at room temperature overnight. Concentrate in vacuo to a residue, add $CH_2Cl_2$, and wash with 0.25 N NaOH (aqueous), water, then brine. Dry over $Na_2SO_4$ and concentrate in vacuo to give 9.46 g of the crude product. Chromatograph (silica gel, 5% MeOH/$CH_2Cl_2$+$NH_3$) to give 3.59 g of the title compound, as a racemate. $^1$H NMR ($CDCl_3$, 200 MHz): 8.43 (d, 1H); 7.55 (d, 1H); 7.45 (d, 1H); 7.11 (d, 1H); 5.31 (s, 1H); 4.86–4.65 (m, 1H); 3.57–3.40 (m, 1H); 2.98–2.55 (m, 6H); 2.45–2.20 (m, 5H).

Step G—Separation of Enantiomers:

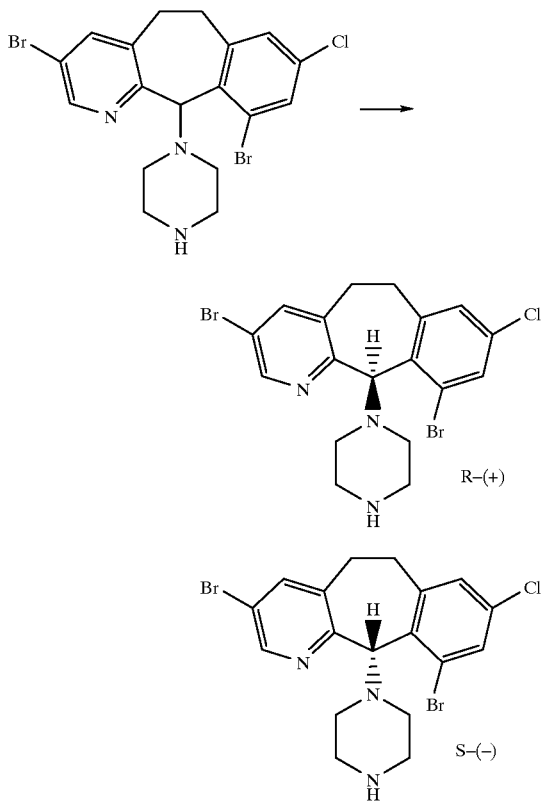

The racemic title compound from Step F (5.7 g) is chromatographed as described for Preparative Example 6, Step D, using 30% iPrOH/hexane+0.2% diethylamine, to give 2.88 g of the R-(+)-isomer and 2.77 g of the S-(−)-isomer of the title compound.

Physical chemical data for the R-(+)-isomer: Mass Spec. MH$^+$=470; $[a]_D^{25}$=+12.10 (10.9 mg/2 mL MeOH).

Physical chemical data for the S-(−)-isomer: Mass Spec. MH$^+$=470; $[a]_D^{25}$=−13.20 (11.51 mg/2 mL MeOH).

PREPARATIVE EXAMPLE 10

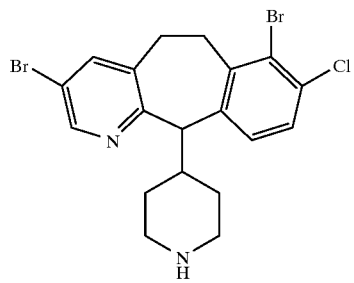

[racemic as well as (+)- and (−)-isomers]

Step A:

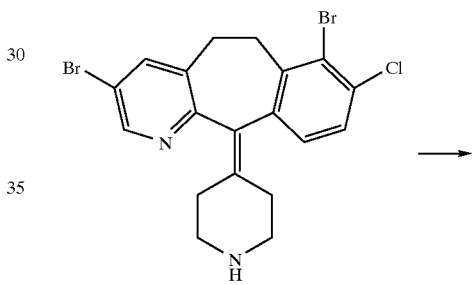

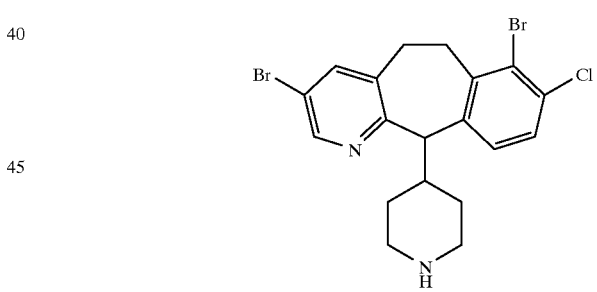

Combine 13 g (33.3 mmol) of the title compound from Preparative Example 4, Step D, and 300 mL of toluene at 20° C., then add 32.5 mL (32.5 mmol) of a 1 M solution of DIBAL in toluene. Heat the mixture at reflux for 1 hr., cool to 20° C., add another 32.5 mL of 1 M DIBAL solution and heat at reflux for 1 hr. Cool the mixture to 20° C. and pour it into a mixture of 400 g of ice, 500 mL of EtOAc and 300 mL of 10% NaOH (aqueous). Extract the aqueous layer with $CH_2Cl_2$ (3×200 mL), dry the organic layers over $MgSO_4$, then concentrate in vacuo to a residue. Chromatograph (silica gel, 12% MeOH/$CH_2Cl_2$+4% $NH_4OH$) to give 10.4 g of the title compound as a racemate. Mass Spec.: MH$^+$=469 (FAB). partial $^1$H NMR ($CDCl_3$, 400 MHz): 8.38 (s, 1H); 7.57 (s, 1H); 7.27 (d, 1H); 7.06 (d, 1H); 3.95 (d, 1H).

Step B—Separation of Enantiomers:

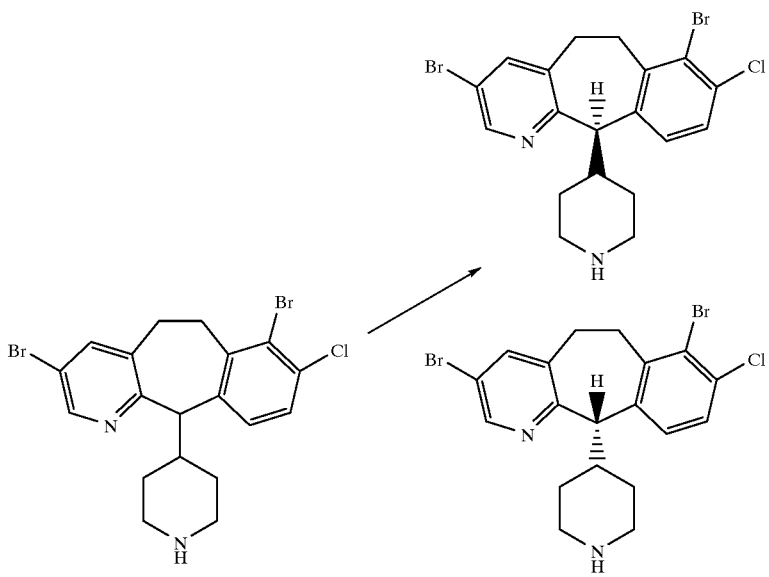

The racemic title compound of Step A is separated by preparative chiral chromatography (Chiralpack AD, 5 cm×50 cm column, using 5% iPrOH/hexane+0.2% diethylamine), to give the (+)-isomer and the (−)-isomer of the title compound.

Physical chemical data for (+)-isomer: Mass Spec. MH$^+$= 470.9 (FAB); $[a]_D^{25}$+43.50 (c=0.402, EtOH); partial $^1$H NMR (CDCl$_3$, 400 MHz): 8.38 (s,1H); 7.57 (s,1H); 7.27 (d,1H); 7.05 (d,1H); 3.95 (d, 1H).

Physical chemical data for (−)-isomer: Mass Spec. MH$^+$= 470.9 (FAB); $[a]_D^{25}$=−41.8° (c=0.328 EtOH); partial $^1$H NMR (CDCl$_3$, 400 MHz): 8.38 (s, 1H); 7.57 (s, 1H); 7.27 (d, 1H); 7.05 (d, 1H); 3.95 (d,1H).

PREPARATIVE EXAMPLE 11

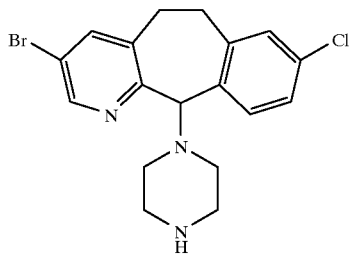

[racemic as well as R-(+)- and S-(−)-isomers]

Treat 4-(8-chloro-3-bromo-5,6-dihydro-11H-benzo[5,6] cyclohepta-[1,2-b]pyridin-11-ylidene)-1-piperidine-1-carboxylic acid ethyl ester via substantially the same procedure as described in Preparative Example 6, Steps A–D, to give as the product of Step C, the racemic title compound, and as the products of Step D the R-(+)-isomer and S-(−)-isomer of the title compound.

Physical chemical data for the R-(+)-isomer: $^{13}$C NMR (CDCl$_3$): 155.8 (C); 146.4 (CH); 140.5 (CH); 140.2 (C); 136.2 (C); 135.3 (C); 133.4 (C); 132.0 (CH); 129.9 (CH); 125.6 (CH); 119.3 (C); 79.1 (CH); 52.3 (CH$_2$); 52.3 (CH); 45.6 (CH$_2$); 45.6 (CH$_2$); 30.0 (CH$_2$); 29.8 (CH$_2$). $[a]_D^{25}$=+ 25.80 (8.46 mg/2 mL MeOH).

Physical chemical data for the S-(−)-isomer: $^{13}$C NMR (CDCl$_3$): 155.9 (C); 146.4 (CH); 140.5 (CH); 140.2 (C); 136.2 (C); 135.3 (C); 133.3(C); 132.0 (CH); 129.9 (CH); 125.5 (CH); 119.2(C); 79.1 (CH); 52.5 (CH$_2$); 52.5 (CH); 45.7 (CH$_2$); 45.7 (CH$_2$); 30.0 (CH$_2$); 29.8 (CH$_2$). $[a]_D^{25}$=− 27.90 (8.90 mg/2 mL MeOH).

PREPARATIVE EXAMPLE 12

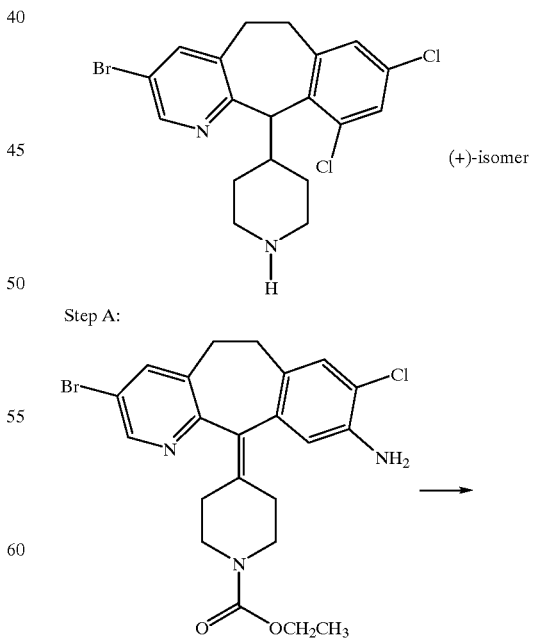

Step A:

-continued

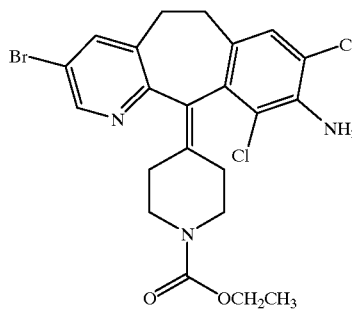

Dissolve 9.90 g (18.9 mmol) of the product of Preparative Example 7, Step B, in 150 mL CH$_2$Cl$_2$ and 200 mL of CH$_3$CN and heat to 60° C. Add 2.77 g (20.8 mmol) N-chlorosuccinimide and heat to reflux for 3 h., monitoring the reaction by TCL (30%EtOAc/H$_2$O). Add an additional 2.35 g (10.4 mmol) of N-chlorosuccinimide and reflux an additional 45 min. Cool the reaction mixture to room temperature and extract with 1 N NaOH and CH$_2$Cl$_2$. Dry the CH$_2$Cl$_2$ layer over MgSO$_4$, filter and purify by flash chromatography (1200 mL normal phase silica gel, eluting with 30% EtOAc/H$_2$O) to obtain 6.24 g of the desired product. M.p. 193–195.4° C.

Step B:

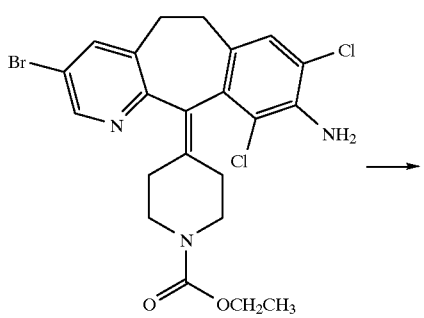

To 160 mL of conc. HCl at −10° C. add 2.07 g (30.1 mmol) NaNO$_2$ and stir for 10 min. Add 5.18 g (10.1 mmol) of the product of Step A and warm the reaction mixture from −10° C. to 0° C. for 2 h. Cool the reaction to −10° C., add 100 mL H$_3$PO$_2$ and let stand overnight. To extract the reaction mixture, pour over crushed ice and basifiy with 50% NaOH/CH$_2$Cl$_2$. Dry the organic layer over MgSO$_4$, filter and concentrate to dryness. Purify by flash chromatography (600 mL normal phase silica gel, eluting with 20% EtOAc/hexane) to obtain 3.98 g of product. Mass spec.: MH$^+$= 497.2.

Step C:

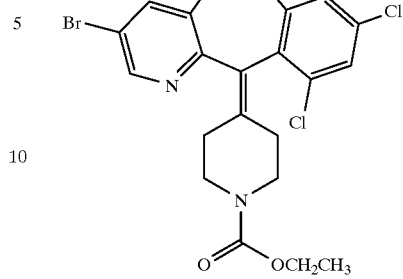

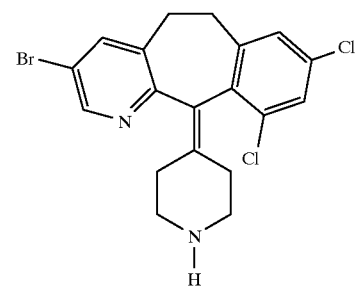

Dissolve 3.9 g of the product of Step B in 100 mL conc. HCl and reflux overnight. Cool the mixture, basify with 50% w/w NaOH and extract the resultant mixture with CH$_2$Cl$_2$. Dry the CH$_2$Cl$_2$ layer over MgSO$_4$, evaporate the solvent and dry under vacuum to obtain 3.09 g of the desired product. Mass spec.: MH$^+$=424.9.

Step D:

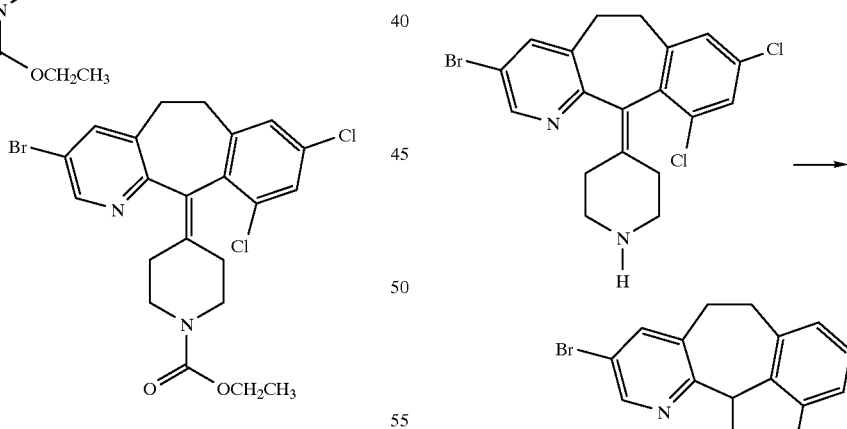

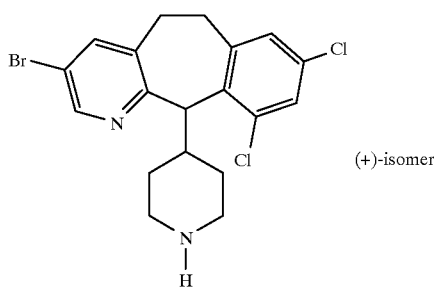
(+)-isomer

Using a procedure similar to that described in Preparative Example 8, obtain 1.73 g of the desired product, m.p. 169.6–170.1° C.; [a]$2_D^{25}$=+48.2° (c=1, MeOH).

EXAMPLE 1

3(R) -[2-(4-(3-bromo-8,10-dichloro-6-11-dihydro-5-H-benzo[5,6]cyclohepta[1,2-b]pyridin-11-yl)-1-piperidinyl]-2-oxoethyl]-1-pyrrolidinecarboxamide

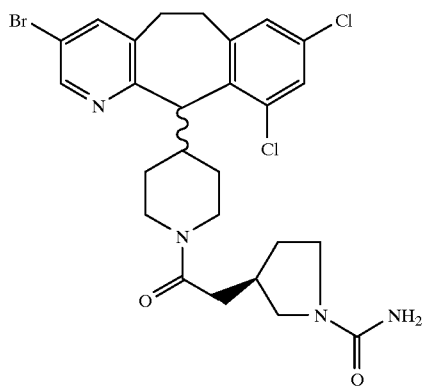

Step 1: 1,1-Dimethylethyl-3(R) -[2-(4-(3-bromo-8,10-dichloro-6-11-dihydro-5-H-benzo[5,6]cyclohepta[1,2-b]pyridin-11-yl)-1-piperidinyl]-2-oxoethyl]-1-pyrrolidinecarboxylate

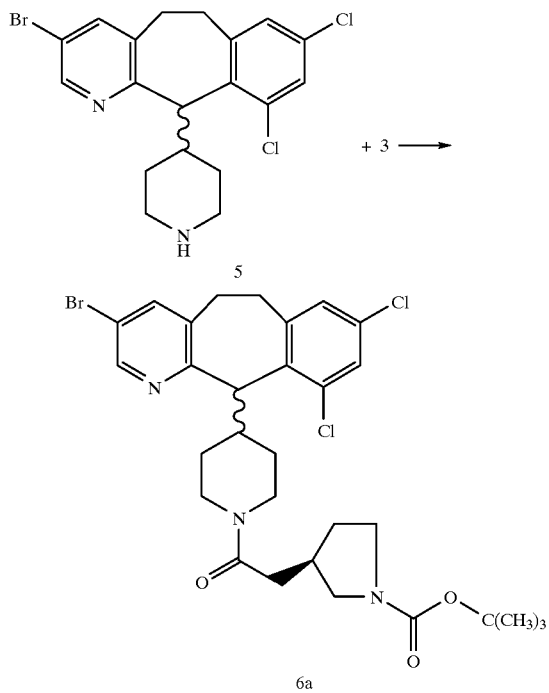

Dissolve 1.0 g (2.34 mmol) of the compound 5 (Preparative Example 12) in 20 ml of DMF, stir at room temperature and add 1.18 g (11.7 mmol) of 4-methylmorpholine, 0.7 g (3.65 mmol) of DEC, 0.494 g (3.65 mmol) of HOBT, and 0.8 g (3.51 mmole) of 3. Stir the mixture at room temperature for 2 days, then concentrate in vacuo to a residue. Partition the residue between $CH_2Cl_2$ and water, wash the organic phase successively with saturated $NaHCO_3$ (aqueous) and brine. Dry the organic phase over $MgSO_4$ and concentrate in in vacuo to a residue. Chromatograph the residue (silica gel, 2% $CH_3OH/CH_2Cl_2+NH_3$) to give 1.15 g of the title compound of Step 1. Mass Spec.: $MH^+$ 639; partial $^1H$ NMR ($CDCl_3$, 200 MHz): 8.42 (d, 1H); 7.45 (s, 1H); 7.28 (d, 1H); 7.08 (s, 1H); 4.88 (d, 1H); 4.45 (d, 1H), 1.45 (s, 9H).

Step 2: 3(R) -[2-(4-(3-bromo-8,10-dichloro-6-11-dihydro-5-H-benzo[5,6]-cyclohepta[1,2-b]pyridin-11-yl)-1-piperidinyl]-2-oxoethyl]-1-pyrrolidine

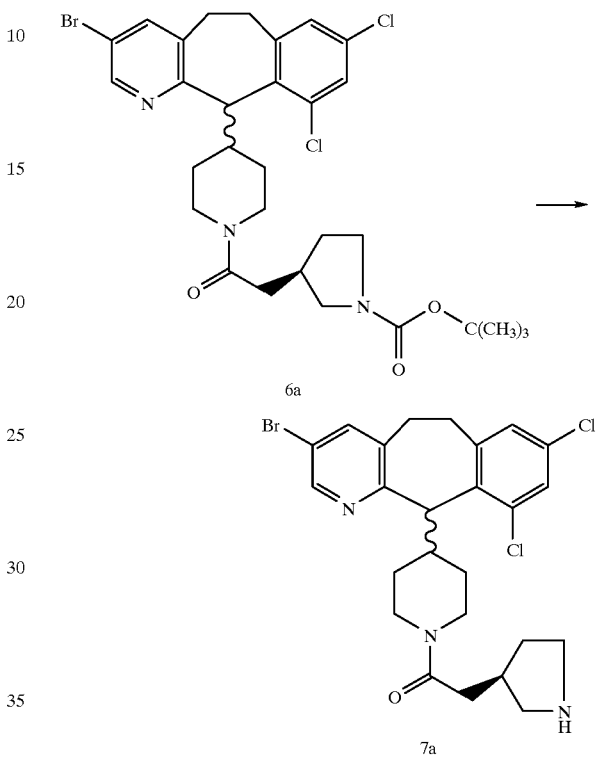

Combine 1.15 g of 6a and 50 mL of $CH_2Cl_2$, cool to 0° C. and add 50 mL of TFA. Stir the mixture for 4 h at 0° C., then concentrate in vacuo. Add water to the resultant residue and adjust to pH 9 with 1 N NaOH (aqueous). Extract with $CH_2Cl_2$, dry over $MgSO_4$ and concentrate in vacuo to give 0.758 g of the product 7a. Mass Spec.: $M^+=538$ (Fab). Partial $^1H$ NMR ($CDCl_3$, 200 MHz): 8.4 (d, 1H); 7.51 (s, 1H); 7.25 (d, 1H); 7.05 (s, 1H); 4.85 (d, 1H); 4.5 (d, 1H).

Step 3:

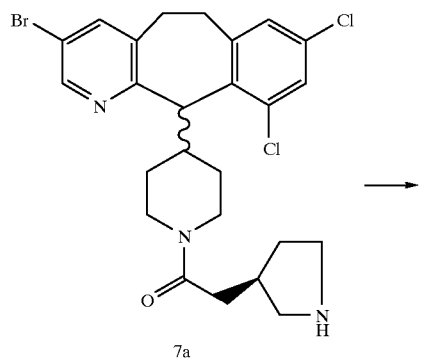

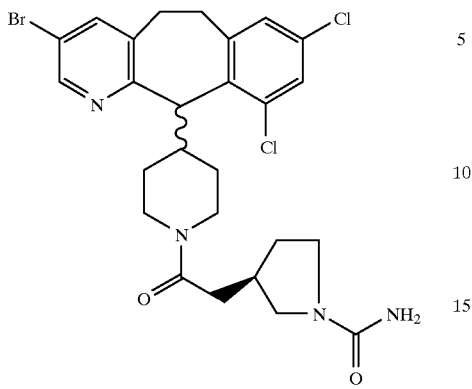

Combine 0.319 g (0.51 mmol) of 7a and 20 mL of CH$_2$Cl$_2$, add 1.6 mL (11.8 mmol) of (CH$_3$)$_3$SiNCO and stir the mixture for 2 days at room temperature. Add 10 mL of NaHCO$_3$ (aqueous), extract with CH$_2$Cl$_2$, wash with brine and dry over MgSO$_4$. Concentrate in vacuo to a residue and chromatograph (silica gel, gradient of 2.5%, 5.0%, then 7.5% CH$_3$OH/CH$_2$Cl$_2$+10% NH$_4$OH) to give 0.196 g of the title compound, m.p=147–150° C.; Mass Spec.: MH$^+$ 580.9 (Fab); partial Partial $^1$H NMR (CDCl$_3$, 200 MHz): 8.45 (d, 1H); 7.52 (s, 1H); 7.3 (d, 1H); 7.1 (s, 1H); 4.85 (d, 1H); 4.52 (d, 1H); 4.35 (bs, 2H).

EXAMPLE 2

3(S) -[2-(4-(3-bromo-8,10-dichloro-6-11-dihydro-5-H-benzo[5,6]-cyclohepta[1,2-b]pyridin-11-yl)-1-piperidinyl]-2-oxoethyl]-1-pyrrolidinecarboxamide

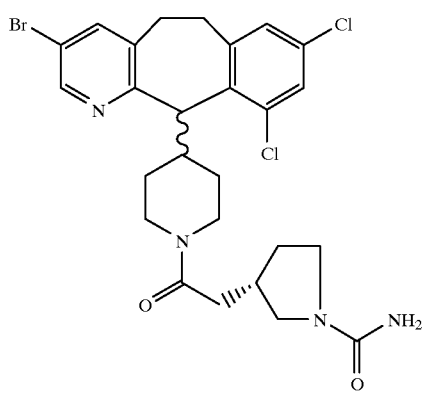

Step 1: 1,1-Dimethylethyl-3(S) -[2-(4-(3-bromo-8,10-dichloro-6-11-dihydro-5-H-benzo[5,6]cyclohepta[1,2-b]pyridin-11-yl)-1-piperidinyl]-2-oxoethyl]-1-pyrrolidinecarboxylate

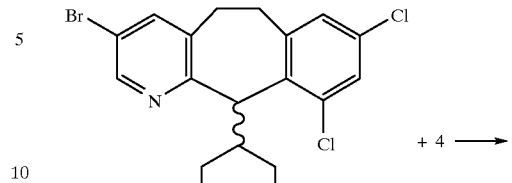

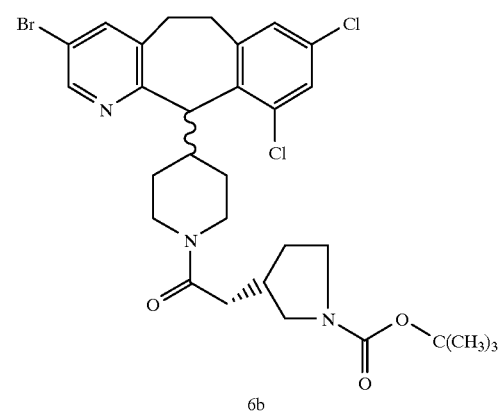

Using the procedure of Example 1, Step 1, except using (S)-(+) 1-N-t-butoxycarbonylpyrrolidinyl-3-acetic acid (4), prepare compound 6b. Mass Spec.: MH$^+$ 639; partial $^1$H NMR (CDCl$_3$, 200 MHz): 8.42(d, 1H); 7.55(s, 1H); 7.30(d, 1H); 7.1 (s, 1H); 4.88(d, 1H); 4.55(d, 1H), 1.45(s, 9H).

Step 2: 3(S)-[2-(4-(3-bromo-8,10-dichloro-6-11-dihydro-5-H-benzo[5,6]-cyclohepta[1,2-b]pyridin-11-yl)-1-piperidinyl]-2-oxoethyl]-1-pyrrolidine

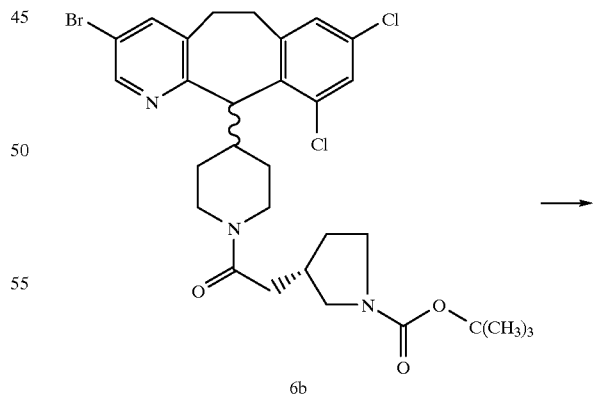

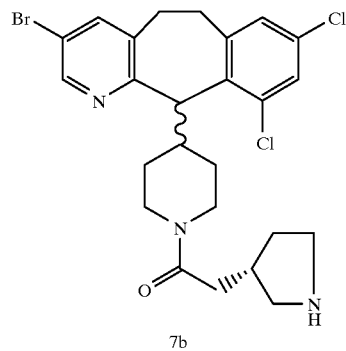

7b

React 1.0 of 6b with 50 mL of TFA using the same procedure as described in Example 1, Step 2, to give 0.66 g of compound 7b. Mass Spec.: M+=538 (Fab). Partial $^1$H NMR (CDCl$_3$, 200 MHz): 8.41 (d, 1H); 7.52 (s, 1H); 7.25 (d,1H); 7.1 (s,1H); 4.85 (d, 1H); 4.52 (d, 1H).

Step 3:

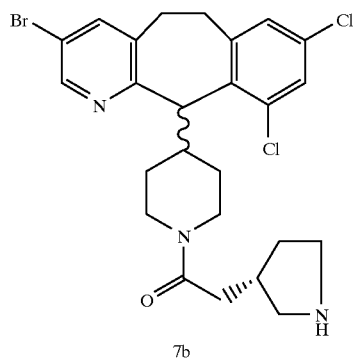

7b

↓

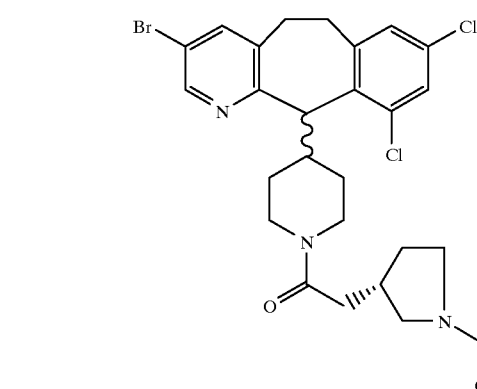

Combine 0.288 g (0.535 mmol) of 7b and 20 mL of CH$_2$Cl2, add 1.44 mL (10.71 mmol) of (CH$_3$)SiNCO and proceed as described in Example 1, Step 3 to give 0.141 g of the title compound, m.p=145–150° C.; Mass Spec.: MH+ 580.9 (Fab); partial Partial $^1$H NMR (CDCl$_3$, 200 MHz): 8.4 (d, 1H); 7.5 (s, 1H); 7.28 (d, 1H); 7.05 (s, 1H); 4.852 (d, 1H); 4.5 (d,1H); 4.35 (bs, 2H).

EXAMPLE 3

3(S)-[2-(4-(3,10-bromo-8-dichloro-6-11-dihydro-5-H-benzo[5,6]-cyclohepta[1,2-b]pyridin-11(R)-yl)-1-piperidinyl]-2-oxoethyl]-1-pyrrolidinecarboxamide

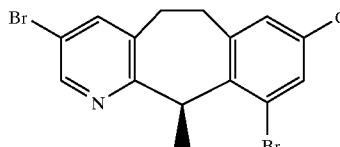

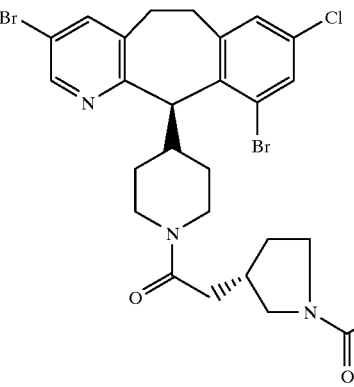

Step 1: 1,1-Dimethylethyl-3(S)-[2-(4-(3,10-dibromo-8-dichloro-6-11-dihydro-5-H-benzo[5,6]cyclohepta[1,2-b]pyridin-11(R)-yl)-1-piperidinyl]-2-oxoethyl]-1-pyrrolidinecarboxylate

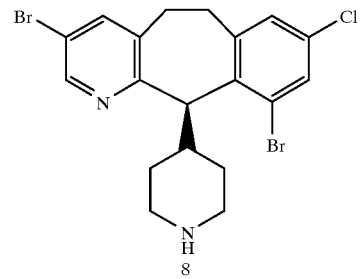

+ 4 →

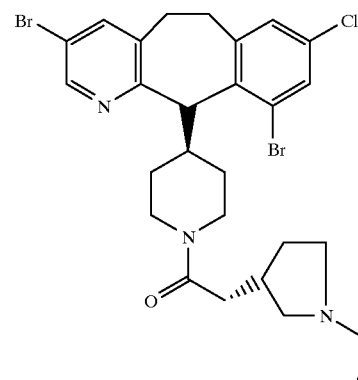

9

React 1.31 g (2.7 mmol) of compound 8 with 0.76 g (3.3 mmol) of compound 4 using substantially same procedure as described in Example 1, Step 1, to give 1.31 g of the product 9. Mass Spec.: M+ 681(Fab). Partial $^1$H NMR (CDCl$_3$, 200 MHz): 8.48 (d, 1H); 7.58 (s, 1H); 5 7.51 (d, 1H); 7.16 (s, 1H); 4.8 (d, 1H); 4.6 (d, 1H), 1.5 (s, 9H).

Step 2: 3(S)-[2-(4-(3,10-dibromo-8-dichloro-6-11-dihydro-5-H-benzo-[5,6]cyclohepta[1,2-b]pyridin-11(R)-yl)-1-piperidinyl]-2-oxoethyl]-1-pyrrolidine

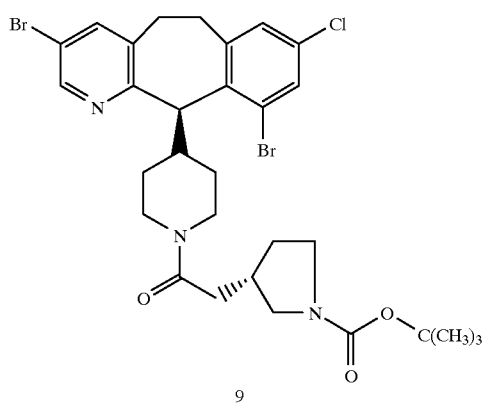

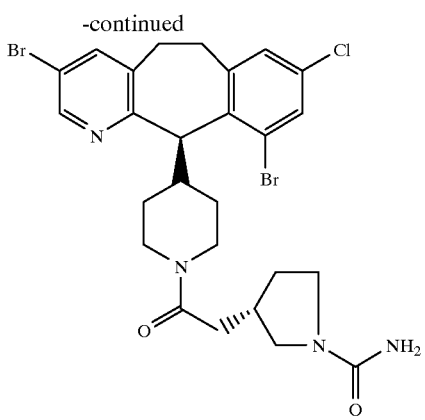

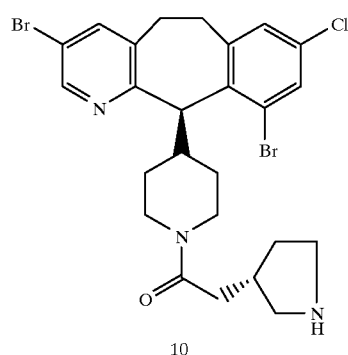

React 1.3 g of 9 with 50 mL of TFA as described in Example 1, Step 2, to give 1.2 g of 10, m.p.=160–162° C.; Mass Spec.: M$^+$=581.9 (Fab). Partial $^1$H NMR (CDCl$_3$, 200 MHz): 8.42 (d, 1H); 7.55 (s,1H); 7.5 (d, 1H); 7.12 (s, 1H); 4.88 (d, 1H); 4.52 (bd, 1H).

Step 3:

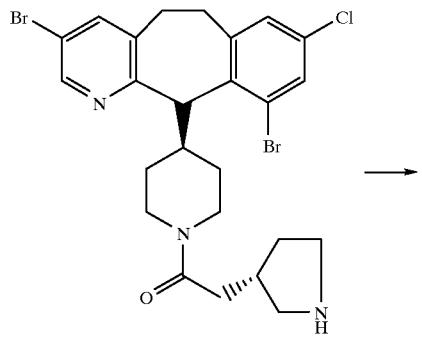

Combine 0.7 g (1.2 mmol) of 10 and 40 mL of CH$_2$Cl$_2$, then add 3.25 mL (24 mmol) of (CH$_3$)SiNCO and proceed as described in Example 1, Step 3 to obtain 0.318 g of the title compound, m.p=148–150° C.; Mass Spec.: MH$^+$ 625 (Fab).

EXAMPLE 4

3(S)-[2-(4-(3,10-bromo-8-dichloro-6-11-dihydro-5-H-benzo[5,6]-cyclohepta[1,2-b]pyridin-11(R)-yl)-1-piperidinyl]-2-oxoethyl]-1-pyrrolidineacetamide

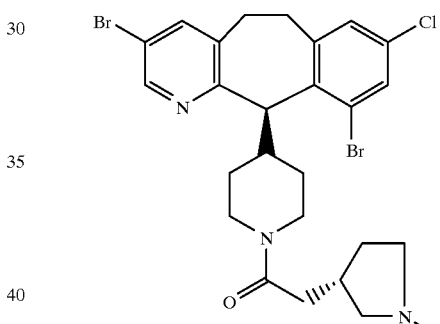

Combine 0.1 g (0.172 mmol) of the product of Example 3, Step 2, 2 mL DMF and 0.036 g (0.339 mmol) Na$_2$CO$_3$ at room temperature, then add 0.0249 g (0.18 mmol) of bromoacetamide and stir the mixture overnight. Add water and filter the solids. Wash the solids with water to give 0.075 g of the product. Mass Spec.: MH$^+$ 639(Fab); Partial $^1$H NMR (CDCl$_3$, 200 MHz): 8.44 (d, 1H); 7.55 (s, 1H); 7.5(d, 1H); 7.15 (s, 1H); 5.5 (bs, 2H); 4.87 (d,1H); 4.5 (d, 1H).

EXAMPLE 5

3(S)-[2-(4-(3,10-bromo-8-dichloro-6-11-dihydro-5-H-benzo[5,6]-cyclohepta[1,2-b]pyridin-11(R)-yl)-1-piperidinyl]-2-oxoethyl]-1-pyrrolidinemethylsulfonamide

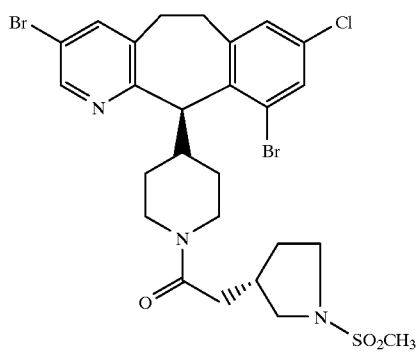

Combine 0.1 g (0.172 mmol) of the product of Example 3, Step 2, 5 mL CH₂Cl₂ and 0.034 g (0.048 mmol) of Et₃N at room temperature, then add 0.021 g (0.189 mmol) of CH₃SO₂Cl and stir the mixture overnight. Evaporate to dryness and purify the resultant residue by preparative chromatography, eluting with EtOAc to give 0.085 g of the product. Mass Spec.: M⁺ 659.9(Fab); Partial ¹H NMR (CDCl₃, 200 MHz): 8.42 (d, 1H); 7.55 (s, 1H); 7.5(d,1H); 7.1 (s, 1H); 5.9 (d, 1H); 4.85 (d,1H); 4.5 (d, 1H); 2.8 (s, 3H).

EXAMPLE 6

2(S)-[2-(4-(3-bromo-8,10-dichloro-6-11-dihydro-5-H-benzo[5,6]cyclohepta[1,2-b]pyridin-11-yl)-1-piperidinyl]-2-oxoethyl]-1-pyrrolidinecarboxamide

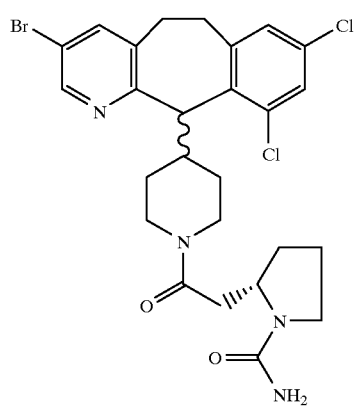

Step 1: 1,1-Dimethylethyl-2(S)-[2-(4-(3-bromo-8,10-dichloro-6-11-dihydro-5-H-benzo[5,6]cyclohepta[1,2-b]pyridin-11-yl)-1-piperidinyl]-2-oxoethyl]-1-pyrrolidinecarboxylate

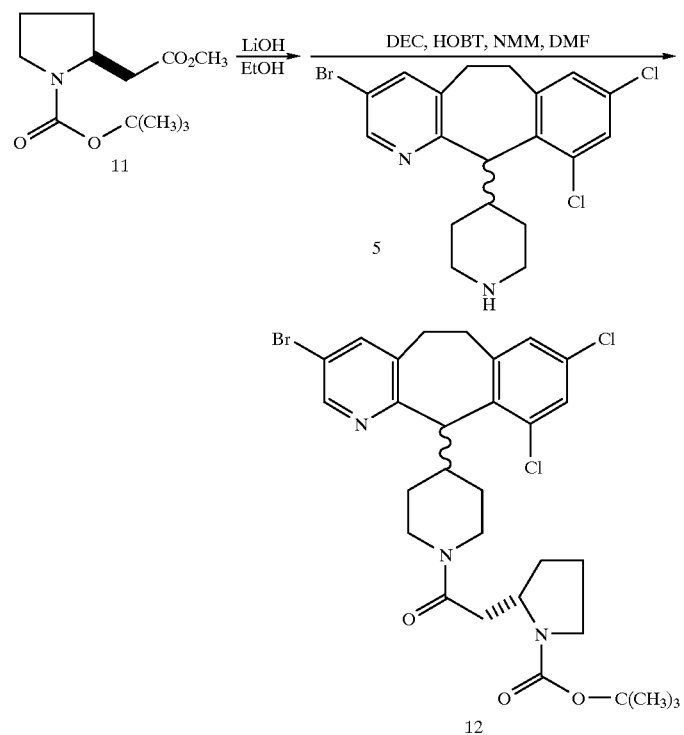

Dissolve N-boc-homoproline methylester (11) (0.56 g, 2.3 mmole) in EtOH (10 mL) and stir with 1 N LiOH (aqueous, 10 mL) at 50° C. overnight. Adjust the pH with 1 N HCl to 4 and evaporate to dryness. Dissolve the residue in DMF (10 mL), and NMM (2 mL) and stir with DEC (0.66 g, 3.44 10 mmole), HOBT (0.47 g, 3.47 mmole), and compound 5 (1.47 g, 3.44 mmole). Evaporate to dryness. Extract with $CH_2Cl_2$ (100 mL) and wash with brine (2×100 mL). Dry over $MgSO_4$ and evaporate to dryness to give an oily product. Flash chromatograph on a silica gel column eluting with 50% hexane/EtOAc to obtain compound 12 (0.95 g), Mass Spec.: $MH^+$ 639; partial $^1H$ NMR ($CDCl_3$, 200 MHz): 8.42 (d, 1H); 7.54 (s, 1H); 7.31 (d, 1H); 7.09 (s,1H); 4.85 (d,1H); 4.53 (d,1H), 1.45 (s, 9H).

Step 2: 2(S)-[2-(4-(3-bromo-8,10-dichloro-6-11-dihydro-5-H-benzo[5,6-]cyclohepta[1,2-b]pyridin-11-yl)-1-piperidinyl]-2-oxoethyl]-1-pyrrolidine

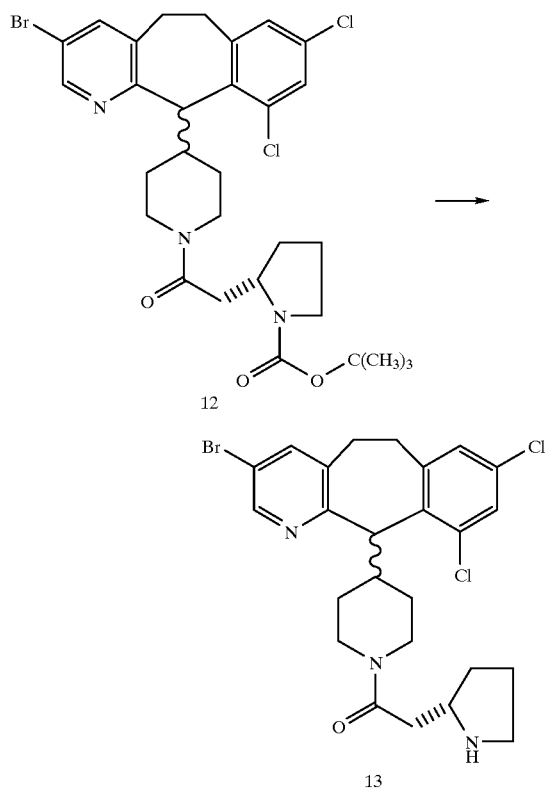

Combine 0.9 g of 12 and 10 mL of $CH_2Cl_2$, then cool to 0° C. and add 10 mL of TFA. Stir the mixture for 3 h at 0° C., then concentrate in vacuo to a residue, add water and adjust the pH to 9 with 1 N NaOH (aqueous). Extract with $CH_2Cl_2$, dry over $MgSO_4$ and concentrate in vacuo to give 0.538 g of 13. Mass Spec.: $M^+$=538 (Fab). Partial $^1H$ NMR ($CDCl_3$, 200 MHz): 8.45(d, 1H); 7.50 (s, 1H); 7.28 (d, 1H); 7.1 (s, 1H); 5 4.88 (d,1H); 4.52 (d,1H).

Step 3:

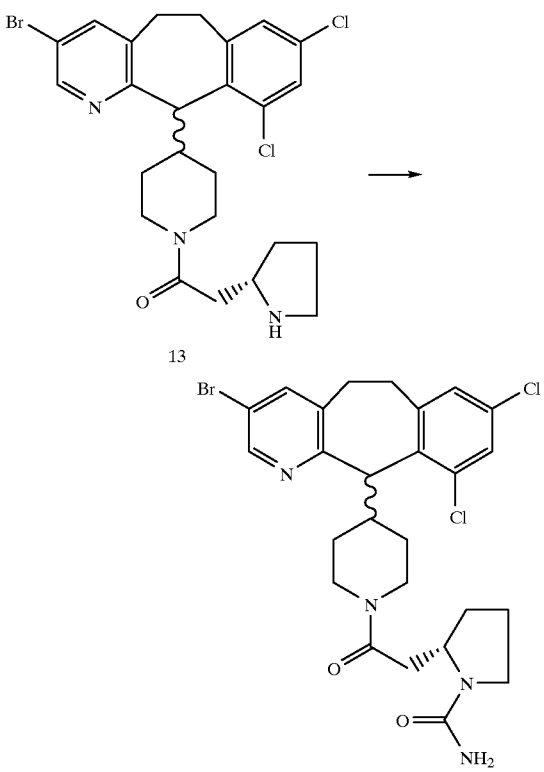

Combine 0.2 g (0.37 mmol) of 13 and 10 mL of $CH_2Cl_2$, add 1.5 mL (11.07 mmol) of $(CH_3)SiNCO$ and stir the mixture overnight at room temperature. Add 10 mL of $NaHCO_3$ (aqueous), then extract with $CH_2Cl_2$, wash with brine and dry over $MgSO_4$. Concentrate in vacuo to a residue and chromatograph (silica gel, gradient of 2.5%, 5.0%, then 7.5% $CH_3OH/CH_2Cl_2$+10% $NH_4OH$) to give 0.132 g of the title compound. Mass Spec.: $MH^+$ 580.9 (Fab); Partial $^1H$ NMR ($CDCl_3$, 200 MHz): 8.4 (d, 1H); 7.5 (s, 1 H); 7.28 (d, 1H); 7.05 (s, 1H); 4.852 (d, 1H); 4.5 (d, 1H); 4.35 (bs, 2H).

EXAMPLE 7

Phenyl 3-[2-[4-(3-bromo-8,10-dichloro-6,11-dihydro-5H benzo[5,6]cyclohepta[1,2-b]pyridin-11-yl)-1-piperidinyl]-2-oxoethyl]-N-cyano-1-pyrrolidinecarboximidate

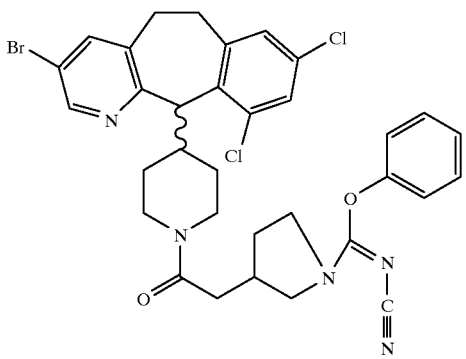

-continued

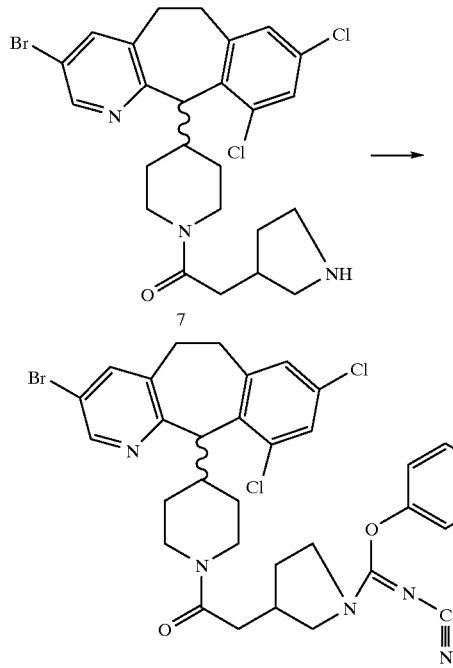

Dissolve compound 7 (1 equivalent) and diphenylcyanocarbonimidate (1.2 equivalents) in 2-propanol and heat the solution at 80° C. under reflux and under $N_2$ for 24 h. Evaporate the mixture to dryness and chromatograph the product on a silica gel column (60×2.5 cm) using neat EtOAc as the eluant to give the title compound.

EXAMPLE 8

3-[2-[4-(3-Bromo-8,10-dichloro-6,11-dihydro-5H-benzo[5,6]cyclohepta[1,2-b]pyridin-11-yl)-1-piperidinyl]-2-oxoethyl]-N-cyano-1-pyrrolidinecarboximidamide

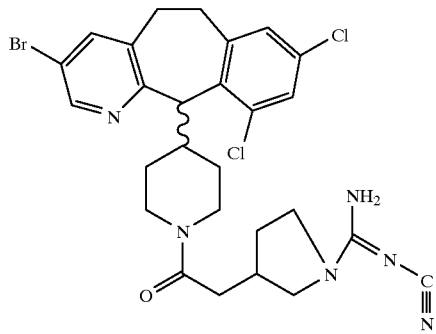

Dissolve the product of Example 7 in 2-propanol and add concentrated $NH_4OH$. Stir the mixture at 25° C. for 24 h and then evaporate to dryness. Triturate the residue with $Et_2O$ (2×250 ml) and discard the ether. Chromatograph the resulting product on a silica gel column using 4% (10% concentrated $NH_4OH$ in $CH_3OH$)—$CH_2Cl_2$ as the eluant to give the title compound.

EXAMPLE 9

Phenyl-3-[2-[4-(3-bromo-8,10-dichloro-6,11-dihydro-5H-benzo[5,6]cyclohepta[1,2-b]pyridin-11-yl)-1-piperidinyl]-2-oxoethyl]-1-pyrrolidinecarboximidate

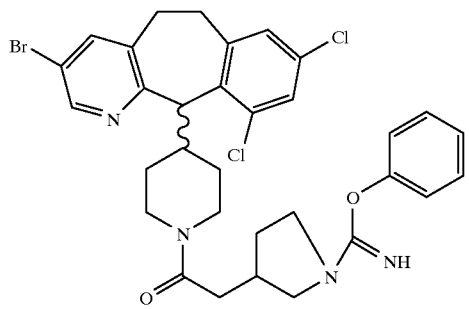

Dissolve compound 7 (1 equivalent) in anhydrous $CH_2Cl_2$, add phenylcyanate (2 equivalents) and diisopropylethylamine (100 drops) and stir the mixture at 25° C. for 15 min. Directly introduce the reaction mixture onto a silica gel column and elute with 10% increasing to 20% (10% concentrated $NH_4OH$ in $CH_3OH$)—$CH_2Cl_2$ to give the title compound.

EXAMPLE 10

1-(3-Bromo-8,10-dichloro-6,11-dihydro-5H-benzo[5,6]-cyclohepta[1,2-b]pyridin-11-yl)-4-[4-(1-cyano-3-pyrrolidinyl)-acetyl]piperidine

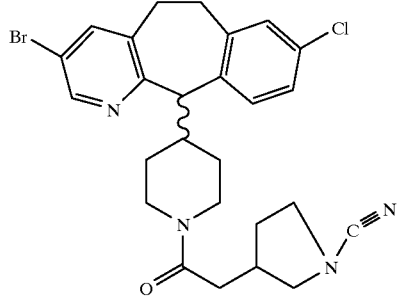

Dissolve the product of Example 9 (1 equivalent) in anhydrous THF. Add a 60% NaH dispersion in oil (4 equivalents) and stir the mixture at 25° C. for 2 h. Dilute the mixture with $CH_2Cl_2$ and wash with 1 .0N NaOH. Dry the $CH_2Cl_2$ layer over $MgSO_4$, filter and evaporate to dryness. Chromatograph the product on a silica gel column eluting with 1.5% (10% concentrated $NH_4OH$ in $CH_3OH$)—$CH_2Cl_2$ to give the title compound.

EXAMPLE 11

Phenyl-3-[2-[4-(3-bromo-8,10-dichloro-6,11-dihydro-5H-benzo[5,6]cyclohepta[1,2-b]pyridin-11-yl)-1-piperidinyl]-2-oxoethyl]-N-sulfamoyl-1-pyrrolidinecarboximidate

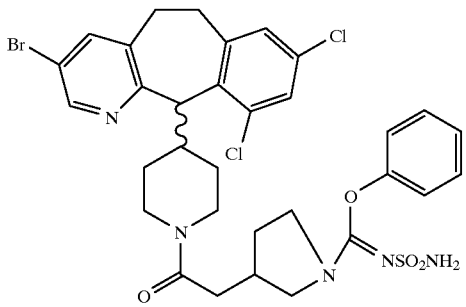

Method 1:

Dissolve compound 7 (1 equivalent) and diphenylsulfamoylcarbonimidate (1.2 equivalents) [prepared as described in: M. Haake and B. Schummelfeder, Synthesis, 753–758 (1991)] in 2-propanol and heat the mixture as described above in Example 7 to give the title compound.

Method 2:

Dissolve the product of Example 9 (1 equivalent) in an inert anhydrous solvent such as $CH_3CN$, benzene or toluene and add $Et_3N$ (2 equivalents). Cool the solution to 0° C. and add sulfamoyl chloride (1.2 equivalents) [prepared as described in: R. Appel and G. Berger, Chem. Ber., 91 (1958), p. 1339–1341]. Stir the mixture at 0° C. to 25° C. for 3 h. Dilute the mixture with $CH_2Cl_2$ and extract with 1 N NaOH. Dry the $CH_2Cl_2$ layer over $MgSO_4$, filter and evaporate to dryness. Chromatograph the product on a silica gel column (15×1 cm) eluting with 2% increasing to 4% (10% concentrated $NH_4OH$ in $CH_3OH$)—$CH_2Cl_2$ to give the title compound.

EXAMPLE 12

3-[2-[4-(3-Bromo-8,10-dichloro-6,11-dihydro-5H-benzo[5,6]cyclohepta[1,2-b]pyridin-11-yl)-1-piperidinyl]-2-oxoethyl]-N-sulfamoyl-1-pyrrolidinecarboximidamide

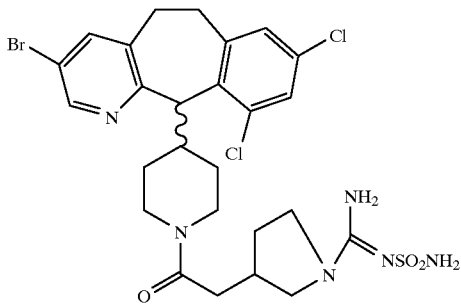

Method 1:

Dissolve the product of Example 11 in 2-propanol and add concentrated $NH_4OH$. Stir the mixture at 25° C. for 24 h and then evaporate to dryness. Triturate the residue with $Et_2O$ (2×250 ml) and discard the ether. The resulting product is chromatographed on a silica gel column to give the title compound.

Alternatively, anhydrous ammonia in a suitable inert solvent such as $CH_3OH$ or THF may be used in place of $NH_4OH$ in the above reaction.

Method 2:

Fuse the product of Example 9 (1 equivalent) with sulfamide (4 to 10 equivalents) at 150° C. to 180° C. for 24 h. Purify the product on a silica gel column to give the title compound.

Alternatively, the reaction may be carried out using a suitable inert solvent such as 2-propanol at reflux temperatures.

Method 3:

Fuse the product of Example 10 (1 equivalent) with sulfamide (4 to 10 equivalents) at 150° C. to 180° C. for 24 h. The product is purified on a silica gel column to give the title compound.

Alternatively, the reaction may be carried out using a suitable inert solvent such as 2-propanol at reflux temperatures.

EXAMPLE 13

Phenyl-3-[2-[4-(3-bromo-8,10-dichloro-6,11-dihydro-5H-benzo[5,6]cyclohepta[1,2-b]pyridin-11-yl)-1-piperidinyl]-2-oxoethyl]-N-(N-methylsulfamoyl)-1-pyrrolidinecarboximidate

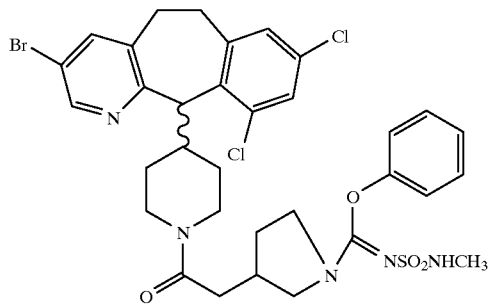

Method 1:

Disolve the product of Example 9 (1 equivalent) in an inert anhydrous solvent such as $CH_3CN$, benzene or toluene and add $Et_3N$ (2 equivalents). Cool the solution to 0° C. and add N-methylsulfamoyl chloride (1.2 equivalents) [prepared as described in: J. A. Kloek and K. L. Leschinsky, J. Org. Chem., 41 (25) (1976), p. 4028–4029]. Stir the mixture at 0° C. to 25° C. for 3 h, extract, filter and evaporate to give the title compound.

Method 2:

Dissolve compound 7 (1 equivalent) and diphenylmethylsulfamoylcarbonimidate (1.2 equivalents) [prepared by the same procedure, only using methylsulfamoyl chloride, as described in: A. Buschauer, Arch. Pharm., 377–378 (1987)] in 2-propanol and heat the mixture as described in Example 7 to give the title compound.

EXAMPLE 14

3-[2-[4-(3-Bromo-8,10-dichloro-6,11-dihydro-5H-benzo[5,6]cyclohepta[1,2-b]pyridin-11-yl)-1-piperridinyl]-2-oxoethyl]-N-(N-methylsulfamoyl)-1-pyrrolidinecarboximidamide

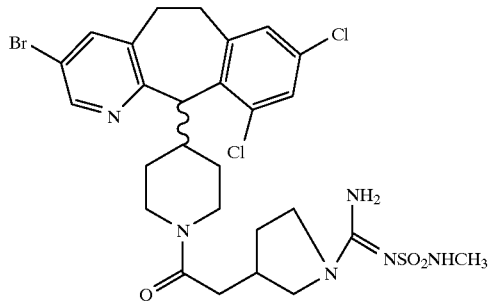

Dissolve the product of Example 13 in 2-propanol and add concentrated $NH_4OH$. Stir the mixture at 25° C. for 24 h and then evaporate to dryness. Triturate the residue with $Et_2O$ (2×250 ml) and discard the ether. The resulting product is chromatographed on a silica gel column to give the title compound.

Alternatively, anhydrous ammonia in a suitable inert solvent such as $CH_3OH$ or THF may be used in place of $NH_4OH$ in the above reaction.

EXAMPLE 15

Phenyl-3-[2-[4-(3-bromo-8,10-dichloro-6,11-dihydro-5H-benzo[5,6]cyclohepta[1,2-b]pyridin-11-yl)-1-piperidinyl]-2-oxoethyl]-N-(N,N-dimethylsulfamoyl)-1-pyrrolidinecarboximidate

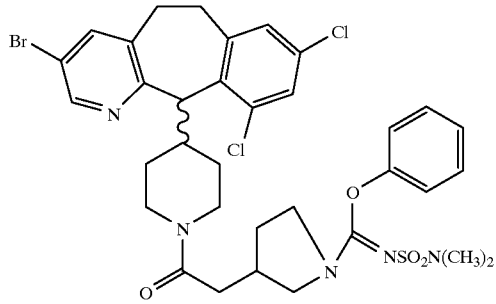

Method 1:

Dissolve the product of Example 9 (1 equivalent) in an inert anhydrous solvent such as $CH_3CN$, benzene or toluene and add $Et_2N$ (2 equivalents). Cool the solution to 0° C. and add N,N-dimethylsulfamoyl chloride (1.2 equivalents). Stir the mixture at 0° C. to 25° C. for 3 h, extract, filter and evaporate to give the title compound.

Method 2:

Dissolve compound 7 (1 equivalent) and diphenyldimethylsulfamoyl-carbonimidate (1.2 equivalents) in 2-propanol and heat the mixture as described in Example 7 to give the title compound.

EXAMPLE 16

Benzo[5,6]cyclohepta[1,2-b]pyridin-11-yl)-1-piperidinyl]-2-oxoethyl]-N-(N,N-dimethylsulfamoyl)-1-pyrrolidinecarboximidamide

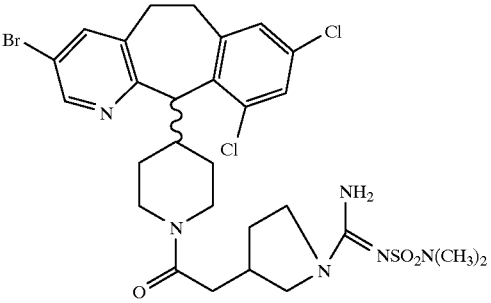

Dissolve the product of Example 15 in 2-propanol and add concentrated $NH_4OH$. Stir the mixture at 25° C. for 24 h and then evaporate to dryness. Triturate the residue with $Et_2O$ (2×250 ml) and discard the ether. The resulting product is chromatographed on a silica gel column to give the title compound.

Alternatively, anhydrous ammonia in a suitable inert solvent such as $CH_3OH$ or THF may be used in place of $NH_4OH$ in the above reaction.

EXAMPLE 17

3-[2-[4-(3-Bromo-8,10-dichloro-6,11-dihydro-5H-benzo[5,6]cyclohepta[1,2-b]pyridin-11-yl)-1-piperidinyl]-2-oxoethyl]-N-hydroxy-1-pyrrolidinecarboximidamide

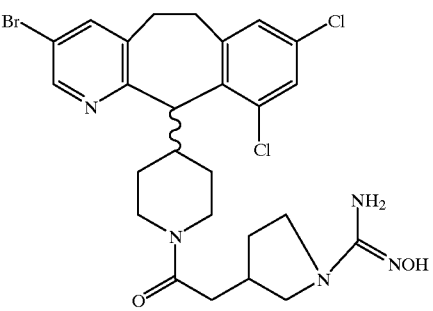

Method 1:

Dissolve the product of Example 9 (1 equivalent) in $CH_3OH$. Prepare an aqueous solution of hydroxylamine by dissolving hydroxylamine hydrochloride (1 equivalent) in 50% (w/v) NaOH (1 equivalent) and add to the mixture; stir at 25° C. for 18 h. Evaporate the solution to dryness and triturate with water. Filter off the solid and purify on silica gel to give the title compound.

Method 2:

Alternatively, the product of Example 10 may be reacted as described in Method 1 above to give the title compound

EXAMPLE 18

3-[2-[4-(3-Bromo-8,10-dichloro-6,11-dihydro-5H-benzo[5,6]cyclohepta[1,2-b]pyridin-1-yl)-1-piperidinyl]-2-oxoethyl]-N-methoxy-1-pyrrolidinecarboximidamide

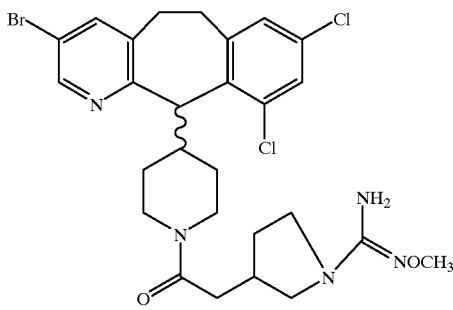

Method 1:

Dissolve the product of Example 9 (1 equivalent) in CH₃OH. Add an aqueous solution of methoxylamine [prepared by dissolving methoxylamine hydrochloride (1 equivalent) in 50% (w/v) NaOH (1 equivalent)] and stir the mixture at 25° C. for 18 h. The solution is evaporated to dryness and triturated with water. The solid is filtered off and purified on silica gel to give the title compound.

Method 2:

The product of Example 9 (1 equivalent) and methoxylamine hydrochloride (1 equivalent) are dissolved in anhydrous pyridine and the mixture is stirred at 25° C. for 2 h. The mixture is evaporated to dryness and purified on silica gel to give the title compound.

EXAMPLE 19

Phenyl-3-[2-[4-(3-bromo-8,10-dichloro-6,11-dihydro-5H-benzo[5,6]cyclohepta[1,2-b]pyridin-11-yl)-1-piperidinyl]-2-oxoethyl]-N-carboxamido-1-pyrrolidinecarboximidate

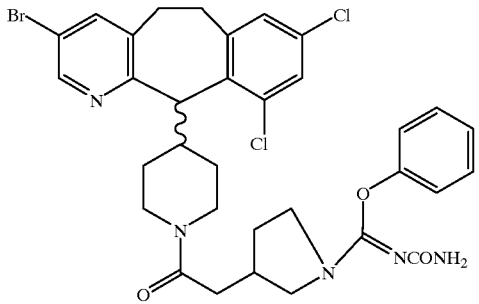

Compound 7 (1 equivalent) and diphenylcarboxamidocarbonimidate (1.2 equivalents) [prepared, using urea in place of sulfamide, as described in: M. Haake and B. Schummelfeder, Synthesis, 753–758 (1991)] are dissolved in 2-propanol and the solution is heated at 80° C. under reflux and under nitrogen for 24 h. The mixture is evaporated to dryness and chromatographed on a silica gel column to give the title compound.

EXAMPLE 20

3-[2-[4-(3-Bromo-8,10-dichloro-6,11-dihydro-5H-benzo[5,6]cyclohepta[1,2-b]pyridin-11-yl)-1-piperidinyl]-2-oxoethyl]-N-carboxamido-1-pyrrolidinecarboximidamide

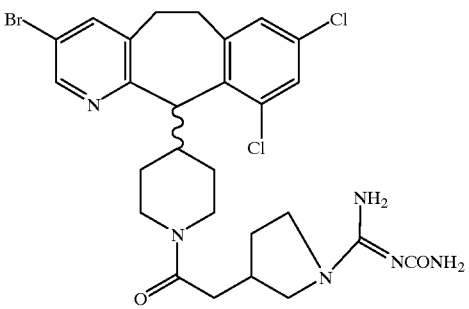

The product of Example 19 is dissolved in 2-propanol and concentrated NH₄OH is added. The mixture is stirred at 25° C. for 24 h and then evaporated to dryness. The residue is triturated with Et₂O (2×250 ml) and the ether discarded. The resulting product is chromatographed on a silica gel column to give the title compound.

Alternatively, anhydrous ammonia in a suitable inert solvent such as CH₃OH or THF may be used in place of NH₄OH in the above reaction.

EXAMPLE 21

Phenyl-3-[2-[4-(3-bromo-8,10-chloro-6,11-dihydro-5H-benzo[5,6]cyclohepta[1,2-b]pyridin-11-yl)-1-piperidinyl]-2-oxoethyl]-N-(N'-methylcarboxamido)-1-pyrrolidinecarboximidate

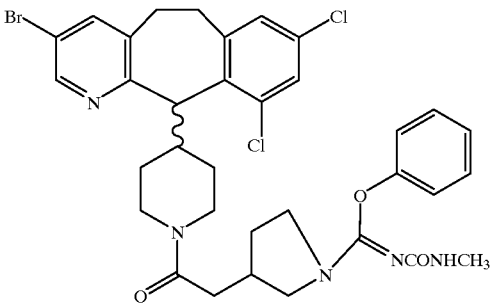

The product of Example 9 (1 equivalent) is dissolved in anhydrous CH₂Cl₂. Methylisocyanate (2 equivalents) is added and the mixture is stirred at 25° C. for 48 h. The mixture is worked up as in Example 19, Method 2, to give the title compound after chromatography on silica gel.

EXAMPLE 22

3-[2-[4-(3-Bromo-8,10-dichloro-6,11-dihydro-5H-benzo[5,6]cyclohepta[1,2-b]pyridin-11-yl)-1-piperidinyl]-2-oxoethyl]-N-(N'-methylcarboxamido)-1-pyrrolidinecarboximidamide

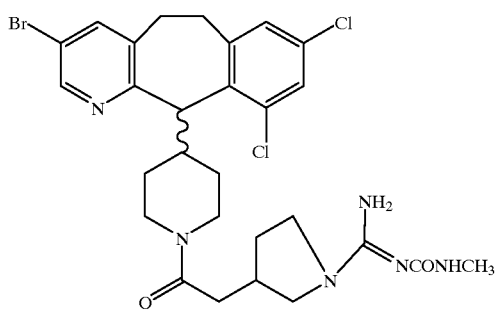

The product of Example 21 is dissolved in 2-propanol and concentrated NH₄OH is added. The mixture is stirred at 25° C. for 24 h and then evaporated to dryness. The residue is triturated with Et₂O (2×250 ml) and the ether discarded. The remaining product is chromatographed on a silica gel column to give the title compound.

Alternatively, anhydrous ammonia in a suitable inert solvent such as CH₃OH or THF may be used in place of NH₄OH in the above reaction.

EXAMPLE 23

5-[3-[2-[4-(3-Bromo-8,10-dichloro-6,11-dihydro-5H-benzo[5,6]cyclohepta[1,2-b]pyridin-11-yl)-1-piperidinyl]-2-oxoethyl]-1-pyrrolidinyl]-3-amino-1,2,4-triazole

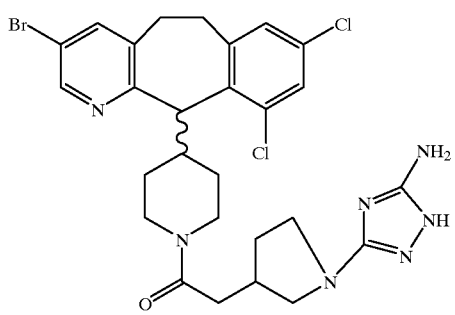

The product of Example 7 (1 equivalent) is dissolved in CH₃OH. Hydrazine hydrate (1 equivalent) is added and the mixture is stirred at 25° C. for 1 h. The mixture is evaporated to dryness and chromatographed on silica gel to give the title compound.

EXAMPLE 24

3-[3-[2-[4-(3-Bromo-8,10-dichloro-6,11-dihydro-5H-benzo[5,6]cyclohepta[1,2-b]pyridin-11-yl)-1-piperidinyl]-2-oxoethyl]-1-pyrrolidinyl]-5-amino-1,2,4-oxadiazole and 5-[3-[2-[4-(3-Bromo-8,10-dichloro-6,11-dihydro-5H-benzo[5,6]cyclohepta[1,2-b]pyridin-11-yl)-1-piperidinyl]-2-oxoethyl]-1-pyrrolidinyl]-3-amino-1,2,4-oxadiazole

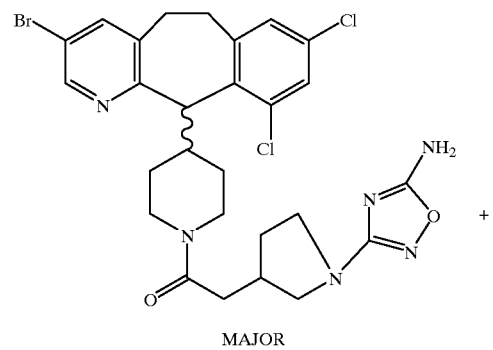

MAJOR

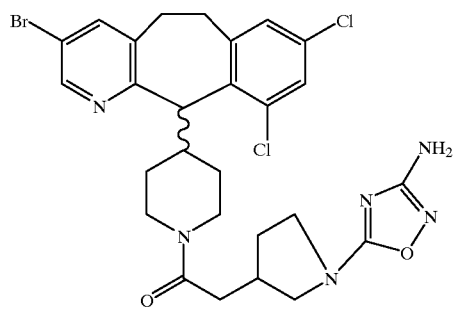

MINOR

The product of Example 10 (1 equivalent) is dissolved in CH₃OH. Hydroxylamine (1 equivalent) is added and the mixture is stirred at 25° C. for 1 h. The mixture is evaporated to dryness and chromatographed on silica gel to give the title compounds.

EXAMPLE 25 n-[3-[2-[4-(-3-Bromo-8,10-dichloro-6,11-dihydro-5H-benzo[5,6]cyclohepta[1,2-b]pyridin-11-yl)-1-piperidinyl]-2-oxoethyl]-1-pyrrolidinyl]-N'-methyl-2-nitro-1-etheneamine

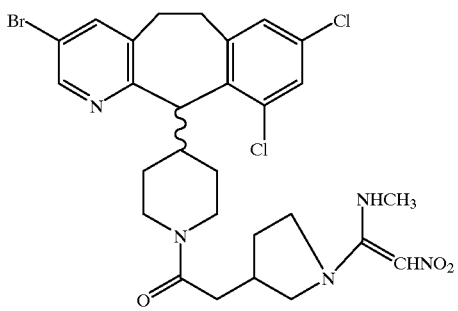

Copper(I)chloride (1 equivalent) is dissolved in anhydrous CH₃CN. To this solution, a solution of compound 7 (1 equivalent), 1-methylthio-1-methylamino-2-nitroethene (1 equivalent) and Et₃N in anhydrous CH₃CN is added dropwise over 10 minutes with stirring. The solid is filtered off, the volume is reduced and CH₂Cl₂ is added. The mixture is washed with aqueous NaHCO₃ and the CH₂Cl₂ layer is dried over MgSO₄, filtered and evaporated to dryness. The residue is purified on silica gel to give the title compound.

EXAMPLE 26

Phenyl-3-[2-[4-(3-Bromo-8,10-dichloro-6,11-dihydro-5H-benzo[5,6]cyclohepta[1,2-b]pyridin-11-yl)-1-piperidinyl]-2-oxoethyl]-N-(methylsulfonyl)-1-pyrrolidinecarboximidate

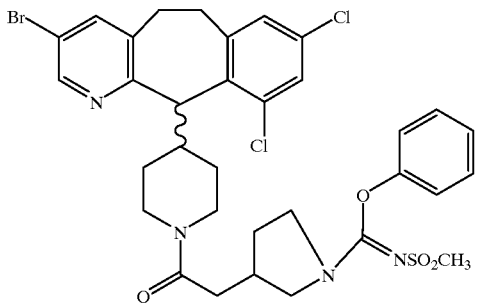

Compound 7 (1 equivalent) and diphenylmethylsulfonylcarbonimidate (1.2 equivalents) [prepared as described in: A. Buschauer, Arch. Pharm., 377–378 (1987)] are dissolved in 2-propanol and the mixture is heated as described in Example 7 to give the title compound.

EXAMPLE 27

3-[2-[4-(3-Bromo-8,10-dichloro-6,11-dihydro-5H-benzo[5,6]cyclohepta[1,2-b]pyridin-11-yl)-1-piperidinyl]-2-oxoethyl]-N-(methylsulfonyl)-1-pyrrolidinecarboximidamide

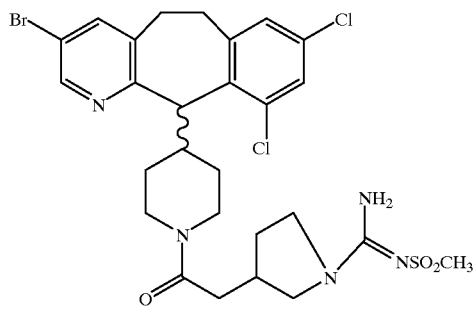

The product of Example 26 is dissolved in 2-propanol and concentrated NH₄OH is added. The mixture is stirred at 25° C. for 24 h and then evaporated to dryness. The residue is triturated with Et₂O (2×250 ml) and the ether discarded. The resulting product is chromatographed on a silica gel column to give the title compound.

Alternatively, anhydrous ammonia in a suitable inert solvent such as CH₃OH or THF may be used in place of NH₄OH in the above reaction.

EXAMPLE 28

Phenyl-3-[2-[4-(3-bromo-8,10-dichloro-6,11-dihydro-5H-benzo[5,6]cyclohepta[1,2-b]pyridin-11-yl)-1-piperidinyl]-2-oxoethyl]-N-benzoyl-1-pyrrolidinecarboximidate Compound 7 (1 equivalent) and diphenylmethylbenzoylcarbonimidate (1.2 equivalents) [prepared as described in: A. Buschauer, Arch. Pharm., 377–378 (1987)] are dissolved in 2-propanol and the mixture is heated as described in Example 7 to give the title compound.

EXAMPLE 29

3-[2-[4-(3-Bromo-8,10-dichloro-6,11-dihydro-5H-benzo[5,6]cyclohepta[1,2-b]pyridin-11-yl)-1-piperidinyl]-2-oxoethyl]-N-benzoyl-1-pyrrolidinecarboximidamide

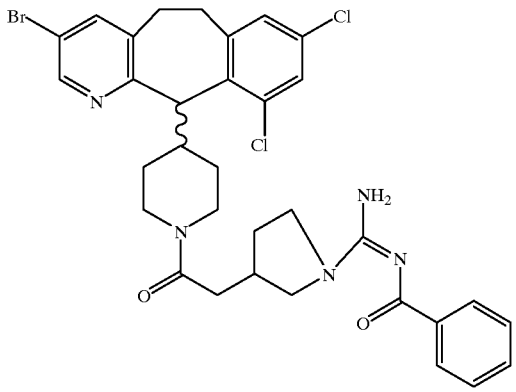

The product of Example 28 is dissolved in 2-propanol and concentrated NH$_4$OH is added. he mixture is stirred at 25° C. for 24 h and then evaporated to dryness. The residue is triturated with Et$_2$O (2×250 ml) and the ether discarded. The resulting product is chromatographed on a silica gel column to give the title compound.

Alternatively, anhydrous ammonia in a suitable inert solvent such as CH$_3$OH or THF may be used in place of NH$_4$OH in the above reaction.

EXAMPLE 30

(+) -4-(3,10-Dibromo-8-chloro-6,11-dihydro-5H-benzo[5,6]-cyclohepta[1,2-b]pyridin-11(R)-yl)-1-[[-1-(4-pyridinyl)-3(S)-pyrrolidinyl]acetyl]piperidine

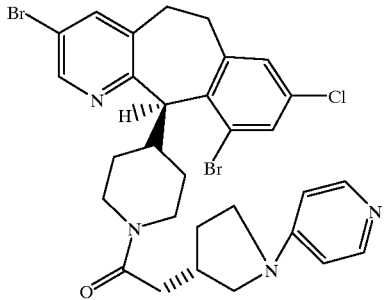

Stir a mixture of compound 10 (1 eq.), anhydrous DMF, 4-chloropyridine hydrochloride (2 eq.) and anhydrous Na$_2$CO$_3$ (2.2 eq.) at 100° C. for 5 days. Cool the mixture to room temperature, dilute with water, filter and wash the solids with water. Dilute the solids with CH$_2$Cl$_2$, wash with 1 M HCl, then with 1 N aqueous NaOH and dry over anhydrous MgSO$_4$. Filter and concentrate in vacuo. Purify by preparative plate chromatography (silica gel) eluting with 5% CH$_3$OH—CH$_2$Cl$_2$ and concentrated NH$_4$OH.

EXAMPLE 31

(+) -4-(3,10-Dibromo-8-chloro-6,11-dihydro-5H-benzo[5,6]cyclohepta[1,2-b]pyridin-11-yl)-1-[[1-(dimethylphosphinyl)-3(S)pyrrolidinyl]acetyl]piperidine

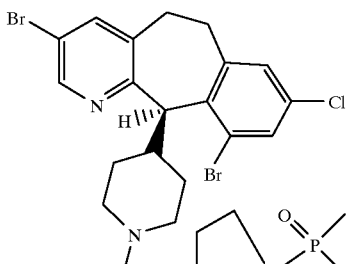

Dissolve compound 10 (1 eq.) and ET$_3$N (5 eq.) in anhydrous CH$_2$Cl$_2$ and add dimethylphosphinyl chloride (4 eq). After stirring at room temperature for 48 h, dilute the solution with CH$_2$Cl$_2$, wash with 1 M HCl, then wash with 1 N aqueous NaOH and dry over anhydrous MgSO$_4$. Filter, concentrate in vacuo and purify the resultant residue by preparative plate chromatography (silica gel) eluting with 2% CH$_3$OH—CH$_2$Cl$_2$ and concentrated NH$_4$OH to provide the title compound.

EXAMPLE 32

(+) -4-(3 10-Dibromo-8-chloro-6,11-dihydro-5H-benzo[5,6]-cyclohepta[1,2-b]pyridin-11-yl)-1-[[1-[2,3,4,6-tetra-o-acetyl-1-beta-D-glucopyranosyl]-3(S)-pyrrolidinyl]acetyl]piperidine

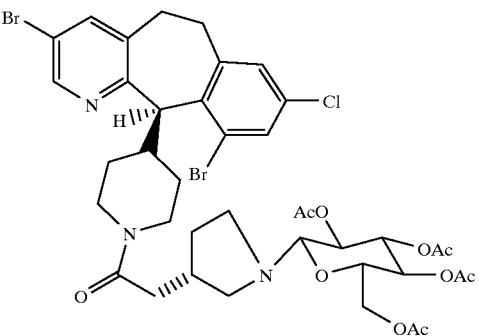

Dissolve compound 10 (1 eq.) in 1,4-dioxane and add anhydrous Na$_2$CO$_3$ (2 eq) and tetraacetoxybromo-alpha-D-glucose (0.15 g, 1.1 eq). After stirring at reflux overnight, concentrate the mixture in vacuo, dilute with CH$_2$Cl$_2$, wash with 1 M HCl, then wash with 1 N aqueous NaOH and dry over anhydrous MgSO$_4$. Filter, concentrate in vacuo and purify the resultant residue by preparative plate chromatography (silica gel) eluting with 2% CH$_3$OH—CH$_2$Cl$_2$ and concentrated NH$_4$OH to provide the title compound.

EXAMPLE 33

3(S)-[2-(4-(3-bromo-8,10-dichloro-6-11-dihydro-5-H-benzo[5,6]cyclohepta[1,2-b]pyridin-11-yl)-1-piperidinyl]-2-oxoethyl]-1-acetylpyrrolidine

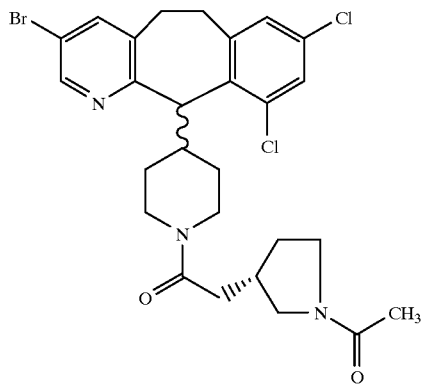

Dissolve compound 7b (1 eq.) in CH$_3$OH and stir with Et$_3$N (2 eq.) and acetic anhydride (2 eq) at room temperature overnight. Evaporate to dryness and chromatograph the residue on a silica gel column eluting with 2% CH$_3$OH—CH$_2$Cl$_2$ and concentrated NH$_4$OH to provide the title compound.

EXAMPLE 34

(+) -1-[[1-(Aminoacetyl)-3(S)-pyrrolididinyl]acetyl]-4-(3,10-dibromo-8-chloro-6,11-dihydro-5H-benzo[5,6]cyclohepta[1,2-b]pyridin-11-yl)piperidine

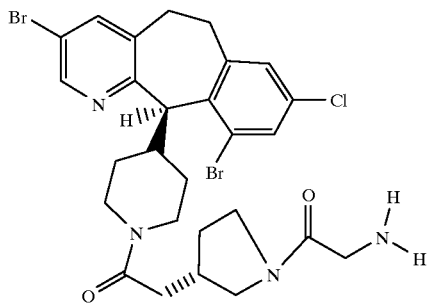

Step 1: (+)-1,1-Dimethylethyl-2-[3(S)-[2-[4-(3,10-dibromo-8-chloro-6,11-dihydro-5H-benzo[5,6]cyclohepta[1,2-b]pyridin-11-yl)-1-piperidinyl]-2-oxoethyl]-1-pyrrolidinyl]-2-oxoethylcarbamate

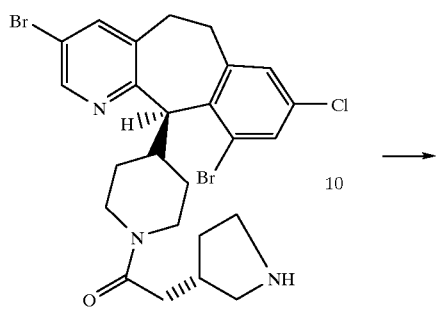

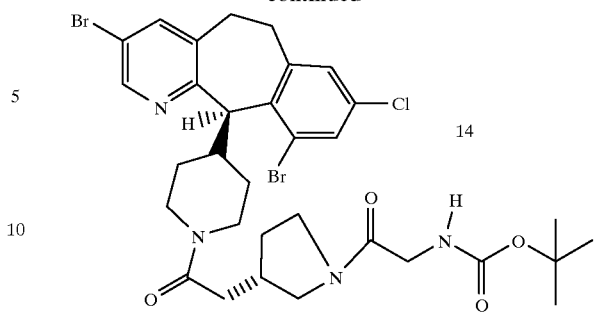

Compound 10 (1 eq) is combined with HOBT (1.5 eq), DEC (1.5 eq), N-BOC-glycine (1.5 eq) and anhydrous DMF and the resulting mixture is stirred at room temperature under nitrogen overnight. The mixture is concentrated in vacuo and the resultant residue diluted with CH$_2$Cl$_2$, washed with 1 M HCl and 1 M aqueous NaOH, then dried over anhydrous MgSO$_4$. Filtration and concentration in vacuo afford compound 14.

Step 2: To compound 14 (1 eq) dissolved in anhydrous CH$_2$Cl$_2$ is added TFA and the resulting solution is stirred at room temperature for 1 hour. 50% aqueous NaOH is added slowly, followed by CH$_2$Cl$_2$ and brine. The mixture is shaken well, the organic phase is separated and dried over anhydrous MgSO$_4$. Filtration and concentration in vacuo afford the title compound

EXAMPLE 35

3(S)-[2-(4-(3-bromo-8,10-dichloro-6-11-dihydro-5-H-benzo[5,6]cyclohepta[1,2-b]pyridin-11-yl)-1-piperidinyl]-2-oxoethyl]-1-methylpyrrolidine

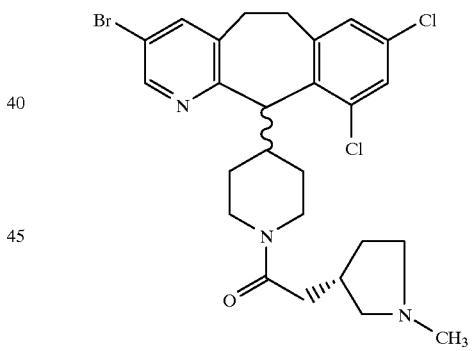

Dissolve compound 7b (1 eq.) in DMF and stir with Et$_3$N (2 eq.) and CH$_3$Br (2 eq) at room temperature overnight. Evaporate to dryness and chromatograph the residue on a silica gel column eluting with 2% CH$_3$OH—CH$_2$Cl$_2$ and concentrated NH$_4$OH to provide the title compound.

ASSAYS

FPT IC$_{50}$ (inhibition of farnesyl protein transferase, in vitro enzyme assay) and COS Cell IC$_{50}$ (Cell-Based Assay) were determined following the assay procedures described in WO 95/10516, published Apr. 20, 1995. GGPT IC$_{50}$ (inhibition of geranylgeranyl protein transferase, in vitro enzyme assay), Cell Mat Assay, and anti-tumor activity (in vivo anti-tumor studies) could be determined by the assay procedures described in WO 95/10516. The disclosure of WO 95/10516 is incorporated herein by reference thereto.

The results are given in Table 1. In Table 1 "Ex. No." stands for "Example Number" and "nM" stands for "nanomolar"

| Ex. No. | FPT IC$_{50}$ (nM) | COS Cell IC$_{50}$ (nM) |
|---|---|---|
| 1 | 0.0386 | — |
| 2 | 0.007 | 0.030 |
| 3 | 0.0036 | — |
| 4 | 0.0029 | — |

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to block tumor growth. The compounds are non-toxic when administered within this dosage range.

The following are examples of pharmaceutical dosage forms which contain a compound of the invention. The scope of the invention in its pharmaceutical composition aspect is not to be limited by the examples provided.

EXAMPLE A

| | Tablets | | |
|---|---|---|---|
| No. | Ingredients | mg/tablet | mg/tablet |
| 1. | Active compound | 100 | 500 |
| 2. | Lactose USP | 122 | 113 |
| | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

EXAMPLE B

| | Capsules | | |
|---|---|---|---|
| No. | Ingredient | mg/capsule | mg/capsule |
| 1. | Active compound | 100 | 500 |
| 2. | Laotose USP | 106 | 123 |
| 3. | Corn Starch, Food Grade | 40 | 70 |
| 4. | Magnesium Stearate NF | 7 | 7 |
| | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:
1. A compound represented by the formula:

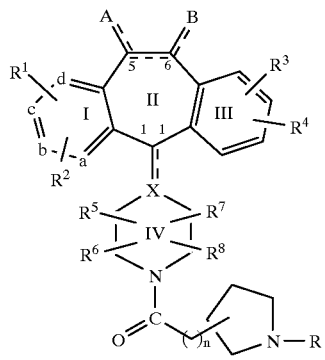

or a pharmaceutically acceptable salt or solvate thereof, wherein: one of a, b, c and d represents N or $NR^9$ wherein $R^9$ is $O^-$, $-CH_3$ or $-(CH_2)_nCO_2H$ wherein n is 1 to 3, and the remaining a, b, c and d groups represent $CR^1$ or $CR^2$; or
  a, b, c, and d are independently selected from the group consisting of $CR^1$ and $CR^2$;
  $R^1$ and $R^2$ are independently selected from the group consisting of H, halo, $-CF_3$, $-OR^{10}$, $-COR^{10}$, $-SR^{10}$, $-S(O)_tR^{11}$ wherein t is 0, 1 or 2, $-SCN$, $-N(R^{10})_2$, $-NR^{10}R^{11}$, $-NO_2$, $-OC(O)R^{10}$, $-CO_2R^{10}$, $-OCO_2R^{11}$, $-CN$, $-NHC(O)R^{10}$, $-NHSO_2R^{10}$, $-CONHR^{10}$, $-CONHCH_2CH_2OH$, $-NR^{10}COOR^{11}$,

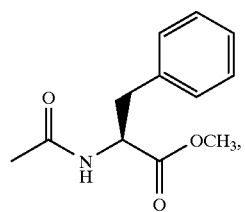

$-SR^{11}C(O)OR^{11}$, $-SR^{11}N(R^{75})_2$ wherein each $R^{75}$ is independently selected from the group consisting of H and $-C(O)OR^{11}$, benzotriazol-1-yloxy, tetrazol-5-ylthio, substituted tetrazol-5-ylthio, alkynyl, alkenyl and alkyl, said alkyl or alkenyl group optionally being substituted with halo, $-OR^{10}$ or $-CO_2R^{10}$;
  $R^3$ and $R^4$ are independently selected from the group consisting of H, $R^1$ and $R^2$, or $R^3$ and $R^4$ taken together represent a saturated or unsaturated $C_5-C_7$ fused ring to the benzene ring;
  $R^5$, $R^6$, $R^7$ and $R^8$ are independently selected from the group consisting of H, $-CF_3$, $-COR^{10}$, alkyl and aryl, said alkyl or aryl optionally being substituted with $-OR^{10}$, $-SR^{10}$, $-S(O)_tR^{11}$, $-NR^{10}COOR^{11}$, $-N(R^{10})_2$, $-NO_2$, $-COR^{10}$, $-OCOR^{10}$, $-OCO_2R^{11}$, $-CO_2R^{10}$ or $OPO_3R^{10}$; or $R^5$ is combined with $R^6$ to represent $=O$ or $=S$; or $R^7$ is combined with $R^8$ to represent $=O$ or $=S$; or $R^5$ is combined with $R^6$ to represent $=O$ or $=S$, and $R^7$ is combined with $R^8$ to represent $=O$ or $=S$;
  $R^{10}$ represents H, alkyl, aryl, or aralkyl;
  $R^{11}$ represents alkyl or aryl;
  X represents N, CH or C, which C may contain an optional double bond (represented by the dotted line) to carbon atom 11;

the dotted line between carbon atoms 5 and 6 represents an optional double bond, such that when a double bond is present, A and B independently are selected from the group consisting of $-R^{10}$, halo, $-OR^{11}$, $-OCO_2R^{11}$ and $-OC(O)R^{10}$, and when no double bond is present between carbon atoms 5 and 6, A and B each independently represent (H, H), ($-OR^{11}$, $-OR^{11}$), (H, halo), (halo, halo), (alkyl, H), (alkyl, alkyl), (H, $-OC(O)R^{10}$), (H, $-OR^{10}$), $=O$, (aryl, H) and $=NOR^{10}$, or A and B together are $-O-(CH_2)_p-O-$ wherein p is 2, 3 or 4; and R represents:
  (1) $-C(O)N(R^{10})_2$;
  (2) $-CH_2C(O)N(R^{10})_2$;
  (3) $-SO_2$-alkyl, $-SO_2$-aryl, $-SO_2$-aralkyl, $-SO_2$-heteroaryl or $-SO_2$-heterocycloalkyl;
  (4) cyano;
  (5) an imidate represented by the formula:

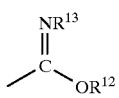

wherein $R^{13}$ is selected from the group consisting of H, CN, $-SO_2$-alkyl, $-C(O)$-aryl, $-SO_2NR^{10}R^{14}$, $-C(O)NR^{10}R^{14}$ and $-OR^{10}$; $R^{12}$ is aryl; and $R^{14}$ is independently selected from the group consisting of H, alkyl, aryl and aralkyl;
  (6) an imidamido group of the formula:

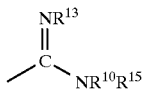

wherein $R^{10}$ and $R^{13}$ are as defined above; $R^{15}$ is alkyl, aryl, aralkyl, cycloalkyl, heteroaryl, heteroaralkyl or heterocycloalkyl;
  (7) a 1-amino-2-nitroethylene derivative of the formula:

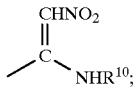

(8) $-C(O)R^{16}$, wherein $R^{16}$ is alkyl, aryl, aralkyl or heteroaryl;
  (9) $-C(O)-O-R^{16}$;

(10)

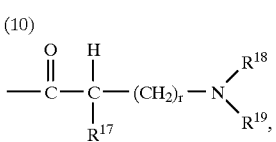

wherein $R^{17}$ is selected from the group consisting of H, alkyl, aralkyl and heteroaralkyl; $R^{18}$ and $R^{19}$ are each independently selected from the group consisting of: H; $-C(O)OR^{20}$, wherein $R^{20}$ represents alkyl, aralkyl, and heteroaralkyl; $-SO_2R^{21}$ wherein $R^{21}$ is selected from the group consisting of alkyl, aryl, aralkyl, heteroaryl and heteroaralkyl; $-C(O)R^{21}$; $C_{1-6}$ alkyl; alkaryl; and $C_{3-6}$ cycloalkyl; and r is 0, 1 or 2;

(11) alkyl, aryl, aralkyl, cycloalkyl, heterocycloalkyl or heteroaryl;

(12) —$SO_2NR^{10}R^{14}$;

(13) —$P(O)(R^{10})_2$;

(14) a sugar group of the formula

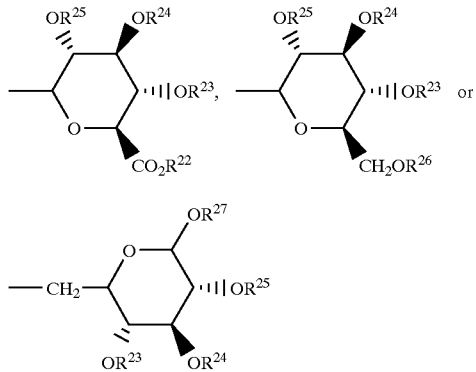

wherein $R^{22}$ and $R^{26}$ are independently selected from the group consisting of H, $(C_1-C_6)$alkyl, aryl and aryl$(C_1-C_6)$alkyl; and $R^{23}$, $R^{24}$, $R^{25}$ and $R^{27}$ are independently selected from the group consisting of H, $(C_1-C_6)$alkyl, aryl$(C_1-C_6)$alkyl, —$C(O)(C_1-C_6)$alkyl and —C(O)aryl; or

(15) —$CH_2C(O)OR^{28}$, wherein $R^{28}$ is selected from the group consisting of H, alkyl, aryl and heteroaryl.

2. A compound of claim 1 wherein $R^2$ is H; $R^1$ is Br or Cl; $R^3$ is Cl or Br; $R^4$ is H, Br or Cl; $R^5$, $R^6$, $R^7$ and $R^8$ are H, A and B are each $H_2$; and the optional double bond between C5 and C6 is absent.

3. A compound of claim 2 wherein $R^4$ is H.

4. A compound of claim 2 wherein $R^4$ is Cl or Br.

5. A compound of claim 4 wherein R is —$C(O)N(R^{10})_2$, —$CH_2C(O)N(R^{10})_2$ or —$SO_2$-alkyl, wherein $R^{10}$ is H and alkyl is methyl.

6. A compound of claim 5 wherein X is CH.

7. A compound of claim 1 represented by the formula

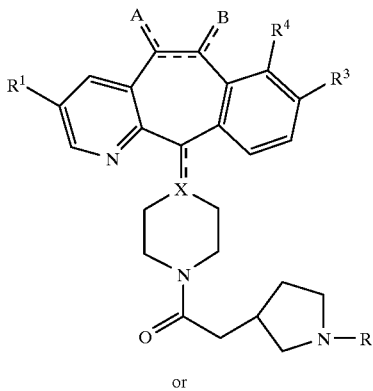

or

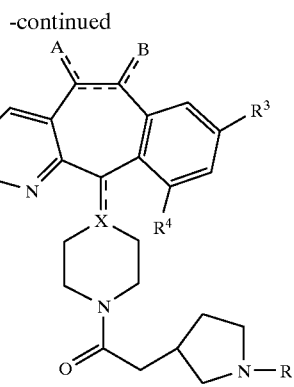

wherein $R^1$, $R^3$ and $R^4$ are independently selected from halo, and A, B, X and R are as defined in claim 1.

8. A compound of claim 7 wherein $R^1$ is Br or Cl; $R^3$ and $R^4$ are independently selected from the group consisting of Br and Cl; A and B are each $H_2$; and the optional bond between C5 and C6 is absent.

9. A compound of claim 8 wherein $R^1$ is Br; $R^3$ is Cl; and $R^4$ is Br or Cl.

10. A compound of claim 9 wherein R is —$C(O)N(R^{10})_2$, —$CH_2C(O)N(R^{10})_2$ or —$SO_2$-alkyl, wherein $R^{10}$ is H and alkyl is methyl.

11. A compound of claim 1 selected from the group consisting of

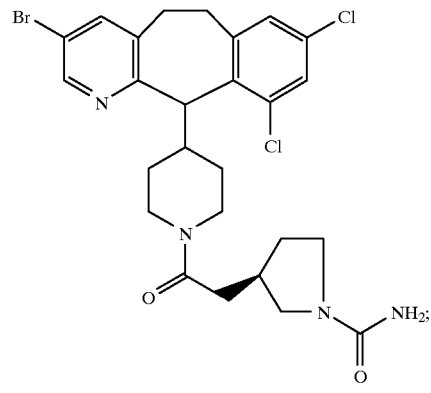

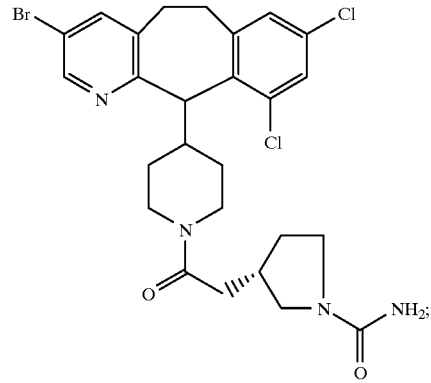

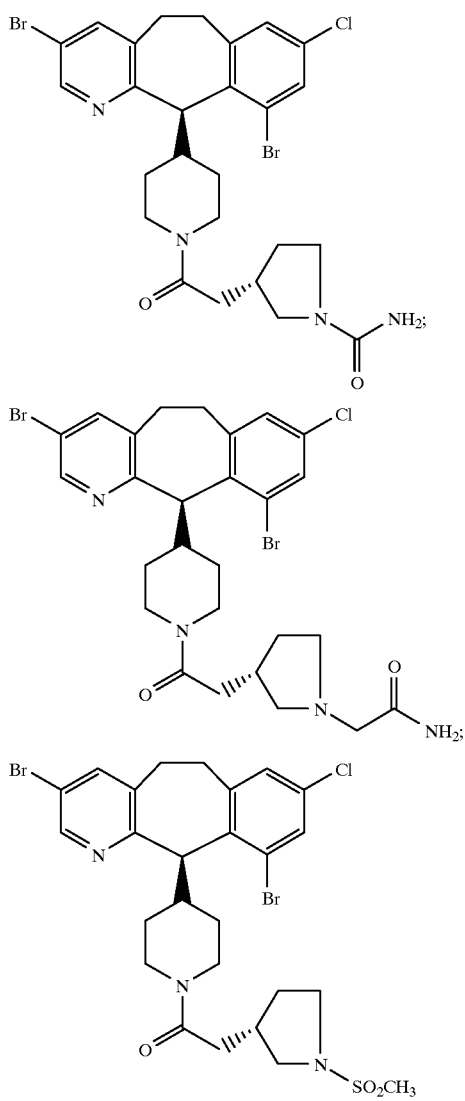

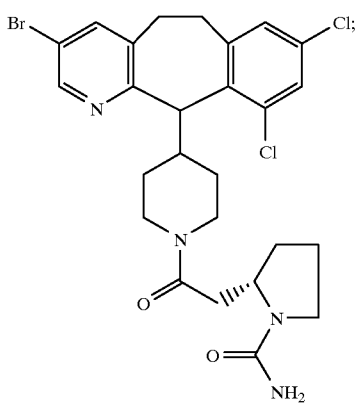

or a pharmaceutically acceptable salt or solvate thereof.

12. A method of treating tumor cells expressing an activated ras oncogene comprising administering an effective amount of a compound of claim 1.

13. The method of claim 12 wherein the cells treated are pancreatic tumor cells, lung cancer cells, myeloid leukemia tumor cells, thyroid follicular tumor cells, myelodysplastic tumor cells, epidermal carcinoma tumor cells, bladder carcinoma tumor cells or colon tumors cells.

14. A method of treating tumor cells wherein the Ras protein is activated as a result of oncogenic mutation in genes other than the Ras gene comprising administering an effective amount of a compound of claim 1.

15. A method of inhibiting farnesyl protein transferase comprising the administration of an effective amount of the compound of claim 1.

16. A pharmaceutical composition comprising an effective amount of compound of claim 1 in combination with a pharmaceutically acceptable carrier.

* * * * *